US012760032B2

(12) United States Patent
Benz et al.

(10) Patent No.: US 12,760,032 B2
(45) Date of Patent: Oct. 13, 2026

(54) HETEROCYCLIC COMPOUNDS

(71) Applicant: Hoffmann-La Roche Inc., Little Falls, NJ (US)

(72) Inventors: Joerg Benz, Rheinfelden (DE); Uwe Grether, Efringen-Kirchen (DE); Benoit Hornsperger, Altkirch (FR); Carsten Kroll, Basel (CH); Bernd Kuhn, Reinach BL (CH); Rainer E. Martin, Basel (CH); Fionn O'Hara, Basel (CH); Hans Richter, Grenzach-Wyhlen (DE); Martin Ritter, Mumpf (CH); Philipp Schmid, Birsfelden (CH)

(73) Assignee: Hoffmann-La Roche Inc., Branchburg, NJ (US)

( * ) Notice: Subject to any disclaimer, the term of this patent is extended or adjusted under 35 U.S.C. 154(b) by 748 days.

(21) Appl. No.: 18/172,506

(22) Filed: Feb. 22, 2023

(65) Prior Publication Data

US 2023/0203056 A1 Jun. 29, 2023

Related U.S. Application Data

(63) Continuation of application No. PCT/EP2021/073313, filed on Aug. 24, 2021.

(30) Foreign Application Priority Data

Aug. 26, 2020 (EP) .................................... 20192867

(51) Int. Cl.

| | |
|---|---|
| ***C07D 491/147*** | (2006.01) |
| ***C07D 487/04*** | (2006.01) |
| *A61P 25/28* | (2006.01) |
| *A61P 29/00* | (2006.01) |
| *A61P 35/00* | (2006.01) |

(52) U.S. Cl.

CPC ....... *C07D 491/147* (2013.01); *C07D 487/04* (2013.01); *A61P 25/28* (2018.01); *A61P 29/00* (2018.01); *A61P 35/00* (2018.01)

(58) Field of Classification Search

CPC ... C07D 491/147; C07D 487/04; A61P 25/28; A61P 29/00; A61P 35/00

See application file for complete search history.

(56) References Cited

U.S. PATENT DOCUMENTS

| | | | |
|---|---|---|---|
| 10,106,556 | B2 | 10/2018 | Ikeda et al. |
| 10,610,520 | B2 | 4/2020 | Ikeda et al. |
| 11,802,133 | B2 | 10/2023 | Bell et al. |
| 11,814,375 | B2 | 11/2023 | Benz et al. |
| 11,981,661 | B2 | 5/2024 | Benz et al. |
| 2020/0255439 | A1 | 8/2020 | Kamata et al. |
| 2022/0135591 | A1 | 5/2022 | Benz et al. |
| 2022/0213093 | A1 | 7/2022 | Benz et al. |
| 2023/0183224 | A1 | 6/2023 | Bell et al. |
| 2024/0150373 | A1 | 5/2024 | Bell et al. |
| 2024/0199587 | A1 | 6/2024 | Amoussa et al. |

FOREIGN PATENT DOCUMENTS

| | | | | |
|---|---|---|---|---|
| WO | 2016/179460 | A1 | 11/2016 | |
| WO | 2017/087854 | A1 | 5/2017 | |
| WO | 2017/171100 | A1 | 10/2017 | |
| WO | 2019/046318 | A1 | 3/2019 | |
| WO | WO-2019180185 | A1 * | 9/2019 | .............. A61P 25/00 |

OTHER PUBLICATIONS

Deng, Hui, and Weimin Li. "Monoacylglycerol Lipase Inhibitors: Modulators for Lipid Metabolism in Cancer Malignancy, Neurological and Metabolic Disorders." Acta Pharmaceutica Sinica B, vol. 10, No. 4, Apr. 2020, pp. 582-602. Science Direct, https://doi.org/10.1016/j.apsb.2019.10.006. (Year: 2020).*

Alpar, A., et al., "Endocannabinoids modulate cortical development by configuring Slit2/Robo1 signaling" Nat Commun 5(4421):1-13 (Jul. 17, 2014).

Bernal-Chico, A., et al., "Blockade of Monoacylglycerol Lipase Inhibits Oligodendrocyte Excitotoxicity and Prevents Demyelination In Vivo" GLIA 63(1):163-176 (Jan. 1, 2015).

Chanda, P.K., et al., "Monoacylglycerol Lipase Activity Is a Critical Modulator of the Tone and Integrity of the Endocannabinoid System" Mol Pharmacol 78(6):996-1003 (Dec. 1, 2010).

Duncan, M., et al., "Review article: endocannabinoids and their receptors in the enteric nervous system" Aliment Pharmacol Ther 22(8):667-683 (Oct. 15, 2005).

Feliu, A., et al., "2-Arachidonoylglycerol Reduces Proteoglycans and Enhances Remyelination in a Progressive Model of Demyelination" J Neurosci 37(35):8385-8398 (Aug. 30, 2017).

Grill, M., et al., "Members of the endocannabinoid system are distinctly regulated in inflammatory bowel disease and colorectal cancer" Sci Rep 9(2358):1-13 (Feb. 20, 2019).

Iannotti, F. A., et al., "Endocannabinoids and endocannabinoid-related mediators: Targets, metabolism and role in neurological disorders" Prog Lipid Res 62:107-128 (Apr. 1, 2016).

(Continued)

*Primary Examiner* — Clinton A Brooks
*Assistant Examiner* — Kyle Nottingham
(74) *Attorney, Agent, or Firm* — Bill Tian Zong-Qiang

(57) ABSTRACT

The invention provides new heterocyclic compounds having the general formula (I)

(I)

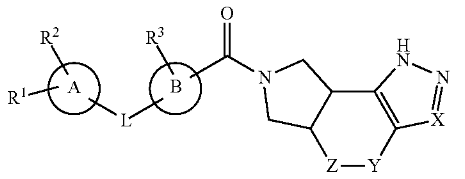

wherein X, Y, Z, A, L, B, and $R^1$ to $R^3$ are as described herein, compositions including the compounds, processes of manufacturing the compounds and methods of using the compounds.

20 Claims, No Drawings

(56) References Cited

OTHER PUBLICATIONS

Ignatowska-Jankowska, B., et al., "Selective Monoacylglycerol Lipase Inhibitors: Antinociceptive versus Cannabimimetic Effects in Mice" J Pharmacol Exp Ther 353(2):424-432 (May 1, 2015).
"International Preliminary Report on Patentability—PCT/EP2021/073313" (Report Issuance Date: Feb. 28, 2023: Chapter I), :pp. 1-7 (Mar. 9, 2023).
"International Search Report—PCT/EP2021/073313" (w/Written Opinion), :pp. 1-10 (Oct. 20, 2021).
Lleo, A., et al., "Molecular targets of non-steroidal anti-inflammatory drugs in neurodegenerative diseases" Cell Mol Life Sci 64(11):1403-1418 (Apr. 20, 2007).
Long, J.Z., et al., "Selective blockade of 2-arachidonoylglycerol hydrolysis produces cannabinoid behavioral effects" Nat Chem Biol 5(1):37-44 (Jan. 1, 2009).
Marquez, L., et al., "Ulcerative Colitis Induces Changes on the Expression of the Endocannabinoid System in the Human Colonic Tissue" PLOS One 4(9):e6893 (1-13) (Sep. 4, 2009).
Mulvihill, M., et al., "Therapeutic Potential of Monoacylglycerol Lipase Inhibitors" Life Sci 92(8-9):492-497 (Nov. 8, 2013).
Nomura, D.K., et al., "Endocannabinoid Hydrolysis Generates Brain Prostaglandins That Promote Neuroinflammation" Science 334(6057):809-813 (Nov. 11, 2011).
Nomura, D.K., et al., "Monoacylglycerol Lipase Exerts Dual Control over Endocannabinoid and Fatty Acid Pathways to Support Prostate Cancer" Chem Biol 18(7):846-856 (Jul. 29, 2011).
Nomura, D.K., et al., "Monoacylglycerol Lipase Regulates a Fatty Acid Network that Promotes Cancer Pathogenesis" Cell 140(1):49-61 (Jan. 8, 2010).
Perisetti, A., et al., "Role of cannabis in inflammatory bowel diseases" Ann Gastroenterol 33(2):134-144 (Feb. 12, 2020).
Qin, H., et al., "The role of monoacylglycerol lipase (MAGL) in the cancer progress" Cell Biochem Biophys 70:33-36 (Mar. 16, 2014).
Viader, A., et al., "Metabolic Interplay between Astrocytes and Neurons Regulates Endocannabinoid Action" Cell Rep 12(5):798-808 (Aug. 4, 2015).
Wang, J., et al., "Effect of monoacylglycerol lipase inhibition on intestinal permeability in chronic stress model" Biochem Biophys Res Commun 525(4):962-967 (May 14, 2020).
Wright, K., et al., "Differential expression of cannabinoid receptors in the human colon: cannabinoids promote epithelial wound healing" Gastroenterology 129(2):437-453 (Aug. 1, 2005).
Yin, J., et al., "ARS2/MAGL signaling in glioblastoma stem cells promotes self-renewal and M2-like polarization of tumor-associated macrophages" Nat Commun 11(1):2978(1-15) (Jun. 12, 2020).
Zhong, P., et al., "Monoacylglycerol Lipase Inhibition Blocks Chronic Stress-Induced Depressive-Like Behaviors via Activation of mTOR Signaling" Neuropsychopharmacology 39(7):1763-1776 (Feb. 19, 2014).

* cited by examiner

HETEROCYCLIC COMPOUNDS

CROSS-REFERENCE TO RELATED APPLICATIONS

This application is a continuation of International Application No. PCT/EP2021/073313, filed Aug. 24, 2021, which claims benefit of priority to European Application No. 20192867.8, filed Aug. 26, 2020, each of which is incorporated herein by reference in its entirety.

FIELD OF THE INVENTION

The present invention relates to organic compounds useful for therapy or prophylaxis in a mammal, and in particular to monoacylglycerol lipase (MAGL) inhibitors for the treatment or prophylaxis of neuroinflammation, neurodegenerative diseases, pain, cancer, mental disorders, multiple sclerosis, Alzheimer's disease, Parkinson's disease, amyotrophic lateral sclerosis, traumatic brain injury, neurotoxicity, stroke, epilepsy, anxiety, migraine, depression, inflammatory bowel disease, abdominal pain, abdominal pain associated with irritable bowel syndrome and/or visceral pain in a mammal.

BACKGROUND OF THE INVENTION

Endocannabinoids (ECs) are signaling lipids that exert their biological actions by interacting with cannabinoid receptors (CBRs), CB1 and CB2. They modulate multiple physiological processes including neuroinflammation, neurodegeneration and tissue regeneration (Iannotti, F. A. et al., *Prog. in Lipid Res.* 2016, 62, 107). In the brain, the main endocannabinoid, 2-arachidonoylglycerol (2-AG), is produced by diacyglycerol lipases (DAGL) and hydrolyzed by the monoacylglycerol lipase, MAGL. MAGL hydrolyses 85% of 2-AG; the remaining 15% being hydrolysed by ABHD6 and ABDH12 (Nomura, D. K. et al., *Science* 2011, 334, 809). MAGL is expressed throughout the brain and in most brain cell types, including neurons, astrocytes, oligodendrocytes and microglia cells (Chanda, P. K. et al., *Mol. Pharmacol.* 2010, 78, 996; Viader, A. et al., *Cell. Rep.* 2015, 12, 798). 2-AG hydrolysis results in the formation of arachidonic acid (AA), the precursor of prostaglandins (PGs) and leukotrienes (LTs). Oxidative metabolism of AA is increased in inflamed tissues. There are two principal enzyme pathways of arachidonic acid oxygenation involved in inflammatory processes, the cyclooxygenase which produces PGs and the 5-lipoxygenase which produces LTs. Of the various cyclooxygenase products formed during inflammation, PGE2 is one of the most important. These products have been detected at sites of inflammation, e.g. in the cerebrospinal fluid of patients suffering from neurodegenerative disorders and are believed to contribute to inflammatory response and disease progression. Mice lacking MAGL (Mgll−/−) exhibit dramatically reduced 2-AG hydrolase activity and elevated 2-AG levels in the nervous system while other arachidonoyl-containing phospho- and neutral lipid species including anandamide (AEA), as well as other free fatty acids, are unaltered. Conversely, levels of AA and AA-derived prostaglandins and other eicosanoids, including prostaglandin E2 (PGE2), D2 (PGD2), F2 (PGF2), and thromboxane B2 (TXB2), are strongly decreased. Phospholipase A2 (PLA2) enzymes have been viewed as the principal source of AA, but cPLA2-deficient mice have unaltered AA levels in their brain, reinforcing the key role of MAGL in the brain for AA production and regulation of the brain inflammatory process.

Neuroinflammation is a common pathological change characteristic of diseases of the brain including, but not restricted to, neurodegenerative diseases (e.g. multiple sclerosis, Alzheimer's disease, Parkinson disease, amyotrophic lateral sclerosis, traumatic brain injury, neurotoxicity, stroke, epilepsy and mental disorders such as anxiety and migraine). In the brain, production of eicosanoids and prostaglandins controls the neuroinflammation process. The pro-inflammatory agent lipopolysaccharide (LPS) produces a robust, time-dependent increase in brain eicosanoids that is markedly blunted in Mgll−/− mice. LPS treatment also induces a widespread elevation in pro-inflammatory cytokines including interleukin-1-a (IL-1-a), IL-1b, IL-6, and tumor necrosis factor-a (TNF-a) that is prevented in Mgll−/− mice.

Neuroinflammation is characterized by the activation of the innate immune cells of the central nervous system, the microglia and the astrocytes. It has been reported that anti-inflammatory drugs can suppress in preclinical models the activation of glia cells and the progression of disease including Alzheimer's disease and mutiple sclerosis (Lleo, A., *Cell. Mol. Life Sci.* 2007, 64, 1403). Importantly, genetic and/or pharmacological disruption of MAGL activity also blocks LPS-induced activation of microglial cells in the brain (Nomura, D. K. et al., *Science* 2011, 334, 809).

In addition, genetic and/or pharmacological disruption of MAGL activity was shown to be protective in several animal models of neurodegeneration including, but not restricted to, Alzheimer's disease, Parkinson's disease and multiple sclerosis. For example, an irreversible MAGL inhibitor has been widely used in preclinical models of neuroinflammation and neurodegeneration (Long, J. Z. et al., *Nat. Chem. Biol.* 2009, 5, 37). Systemic injection of such inhibitor recapitulates the Mgll−/− mice phenotype in the brain, including an increase in 2-AG levels, a reduction in AA levels and related eicosanoids production, as well as the prevention of cytokines production and microglia activation following LPS-induced neuroinflammation (Nomura, D. K. et al., *Science* 2011, 334, 809), altogether confirming that MAGL is a druggable target.

Consecutive to the genetic and/or pharmacological disruption of MAGL activity, the endogenous levels of the MAGL natural substrate in the brain, 2-AG, are increased. 2-AG has been reported to show beneficial effects on pain with, for example, anti-nociceptive effects in mice (Ignatowska-Jankowska, B. et al., *J. Pharmacol. Exp. Ther.* 2015, 353, 424) and on mental disorders, such as depression in chronic stress models (Zhong, P. et al., *Neuropsychopharmacology* 2014, 39, 1763).

Furthermore, oligodendrocytes (OLs), the myelinating cells of the central nervous system, and their precursors (OPCs) express the cannabinoid receptor 2 (CB2) on their membrane. 2-AG is the endogenous ligand of CB1 and CB2 receptors. It has been reported that both cannabinoids and pharmacological inhibition of MAGL attenuate OLs's and OPCs's vulnerability to excitotoxic insults and therefore may be neuroprotective (Bemal-Chico, A. et al., *Glia* 2015, 63, 163). Additionally, pharmacological inhibition of MAGL increases the number of myelinating OLs in the brain of mice, suggesting that MAGL inhibition may promote differentiation of OPCs in myelinating OLs in vivo (Alpar, A. et al., *Nat. Commun.* 2014, 5, 4421). Inhibition of MAGL was also shown to promote remyelination and functional recovery in a mouse model of progressive multiple sclerosis (Feliu, A. et al., *J. Neurosci.* 2017, 37, 8385).

In addition, in recent years, metabolism is talked highly important in cancer research, especially the lipid metabolism. Researchers believe that the de novo fatty acid synthesis plays an important role in tumor development. Many studies illustrated that endocannabinoids have anti-tumorigenic actions, including anti-proliferation, apoptosis induction and anti-metastatic effects. MAGL as an important decomposing enzyme for both lipid metabolism and the endocannabinoids system, additionally as a part of a gene expression signature, contributes to different aspects of tumourigenesis, including in glioblastoma (Qin, H. et al., *Cell Biochem. Biophys.* 2014, 70, 33; Nomura, D. K. et al., *Cell* 2009, 140, 49; Nomura, D. K. et al., *Chem. Biol.* 2011, 18, 846; Jinlong, Y. et al., *Nat. Commun.* 2020, 11, 2978).

The endocannabinoid system is also involved in many gastrointestinal physiological and physiopathological actions (Marquez, L. et al., *PLoS One* 2009, 4, e6893). All these effects are driven mainly via cannabinoid receptors (CBRs), CB1 and CB2. CB1 receptors are present throughout the GI tract of animals and healthy humans, especially in the enteric nervous system (ENS) and the epithelial lining, as well as smooth muscle cells of blood vessels in the colonic wall (Wright, K. et al., *Gastroenterology* 2005, 129, 437; Duncan, M. et al., *Aliment. Pharmacol. Ther.* 2005, 22, 667). Activation of CB1 produces anti-emetic, anti-motility, and anti-inflammatory effect, and help to modulate pain (Perisetti, A. et al., *Ann. Gastroenterol.* 2020, 33, 134). CB2 receptors are expressed in immune cells such as plasma cells and macrophages, in the lamina propria of the GI tract (Wright, K. et al., *Gastroenterology* 2005, 129, 437), and primarily on the epithelium of human colonic tissue associated with inflammatory bowel disease (IBD). Activation of CB2 exerts anti-inflammatory effect by reducing pro-inflammatory cytokines. Expression of MAGL is increased in colonic tissue in UC patients (Marquez, L. et al., *PLoS One* 2009, 4, e6893) and 2-AG levels are increased in plasma of IBD patients (Grill, M. et al., *Sci. Rep.* 2019, 9, 2358). Several animal studies have demonstrated the potential of MAGL inhibitors for symptomatic treatment of IBD. MAGL inhibition prevents TNBS-induced mouse colitis and decreases local and circulating inflammatory markers via a CB1/CB2 MoA (Marquez, L. et al., *PLoS One* 2009, 4, e6893). Furthermore, MAGL inhibition improves gut wall integrity and intestinal permeability via a CB1 driven MoA (Wang, J. et al., *Biochem. Biophys. Res. Commun.* 2020, 525, 962).

In conclusion, suppressing the action and/or the activation of MAGL is a promising new therapeutic strategy for the treatment or prevention of neuroinflammation, neurodegenerative diseases, pain, cancer, mental disorders, inflammatory bowel disease, abdominal pain and abdominal pain associated with irritable bowel syndrome. Furthermore, suppressing the action and/or the activation of MAGL is a promising new therapeutic strategy for providing neuroprotection and myelin regeneration. Accordingly, there is a high unmet medical need for new MAGL inhibitors.

SUMMARY OF THE INVENTION

In a first aspect, the present invention provides a compound of formula (I), or a pharmaceutically acceptable salt thereof, (I)

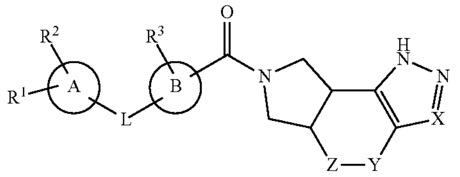

wherein X, Y, Z, A, L, B, and $R^1$ to $R^3$ are as described herein.

In one aspect, the present invention provides a process of manufacturing a compound of formula (IA) or (IB) described herein, comprising:

(a) reacting an amine of formula 2, wherein X, Y, and Z are as described herein,

2

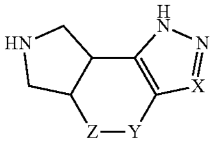

with a carboxylic acid 3a, wherein L, A, B, and $R^1$ to $R^3$ are as described herein 3a

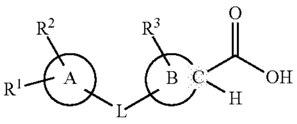

in the presence of a coupling reagent, such as CDI, DCC, HATU, HBTU, HOBT, TBTU, $T_3P$ or Mukaiyama reagent, and optionally in the presence of a base, such as TEA, DIPEA (Huenig's base) or DMAP, to form said compound of formula (IB), wherein X, Y, Z, L, A, B, and $R^1$ to $R^3$ are as defined herein (IB)

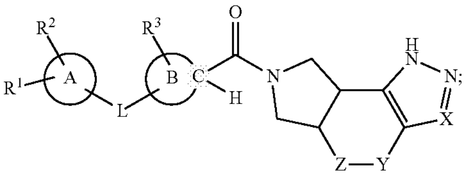

(b) reacting an amine of formula 2, wherein X, Y, and Z are as described herein,

2

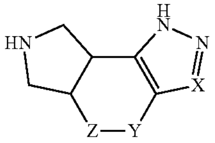

with a carboxylic acid chloride 3b, wherein L, A, B, and $R^1$ to $R^3$ are as described herein 3b

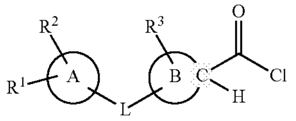

in the presence of a base, such as TEA, Huenig's base, pyridine, DMAP or lithium bis(trimethylsilyl)amide, to form said compound of formula (IB), wherein X, Y, Z, L, A, B, and $R^1$ to $R^3$ are as defined herein; or (c) reacting a first amine of formula 1, wherein A, B, L, and $R^1$ and $R^3$ are as described herein,

1

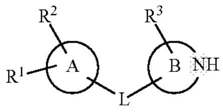

with a second amine 2, wherein X, Y, and Z are as described herein

2

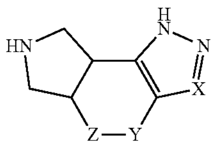

in the presence of a base, such as sodium bicarbonate, and a urea forming reagent, such as bis(trichloromethyl) carbonate, phosgene, trichloromethyl chloroformate, (4-nitrophenyl)carbonate or 1,1'-carbonyldiimidazole, to form said compound of formula (IA), wherein X, Y, Z, L, A, B, and $R^1$ to $R^3$ are as defined herein (IA)

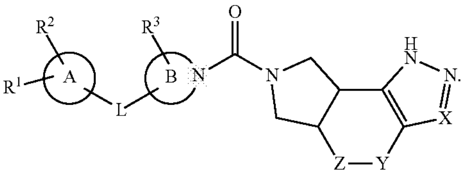

In a further aspect, the present invention provides a compound of formula (I) as described herein, when manufactured according to the processes described herein.

In a further aspect, the present invention provides a compound of formula (I) as described herein, for use as therapeutically active substance.

In a further aspect, the present invention provides a pharmaceutical composition comprising a compound of formula (I) as described herein and a therapeutically inert carrier.

In a further aspect, the present invention provides the use of a compound of formula (I) as described herein or of a pharmaceutical composition described herein for inhibiting monoacylglycerol lipase (MAGL) in a mammal.

In a further aspect, the present invention provides the use of a compound of formula (I) as described herein, or a pharmaceutically acceptable salt thereof, or of a pharmaceutical composition described herein for the treatment or prophylaxis of neuroinflammation, neurodegenerative diseases, pain, cancer, mental disorders and/or inflammatory bowel disease in a mammal.

In a further aspect, the present invention provides the use of a compound of formula (I) as described herein, or a pharmaceutically acceptable salt thereof, or of a pharmaceutical composition described herein for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain, spasticity associated with pain, abdominal pain, abdominal pain associated with irritable bowel syndrome and/or visceral pain in a mammal.

DETAILED DESCRIPTION OF THE INVENTION

Definitions

Features, integers, characteristics, compounds, chemical moieties or groups described in conjunction with a particular aspect, embodiment or example of the invention are to be understood to be applicable to any other aspect, embodiment or example described herein, unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The term "alkyl" refers to a mono- or multivalent, e.g., a mono- or bivalent, linear or branched saturated hydrocarbon group of 1 to 12 carbon atoms. In some preferred embodiments, the alkyl group contains 1 to 6 carbon atoms ("$C_{1-6}$alkyl"), e.g., 1, 2, 3, 4, 5, or 6 carbon atoms. In other embodiments, the alkyl group contains 1 to 3 carbon atoms, e.g., 1, 2 or 3 carbon atoms. Some non-limiting examples of alkyl include methyl, ethyl, propyl, 2-propyl (isopropyl), n-butyl, iso-butyl, sec-butyl, tert-butyl, and 2,2-dimethylpropyl. A particularly preferred, yet non-limiting example of alkyl is methyl.

The term "alkoxy" refers to an alkyl group, as previously defined, attached to the parent molecular moiety via an oxygen atom. Unless otherwise specified, the alkoxy group contains 1 to 12 carbon atoms. In some preferred embodiments, the alkoxy group contains 1 to 6 carbon atoms ("$C_{1-6}$-alkoxy"). In other embodiments, the alkoxy group contains 1 to 4 carbon atoms. In still other embodiments, the alkoxy group contains 1 to 3 carbon atoms. Some non-limiting examples of alkoxy groups include methoxy, ethoxy, n-propoxy, isopropoxy, n-butoxy, isobutoxy and tert-butoxy. A particularly preferred, yet non-limiting example of alkoxy is methoxy.

The term "halogen" or "halo" refers to fluoro (F), chloro (Cl), bromo (Br), or iodo (I). Preferably, the term "halogen" or "halo" refers to fluoro (F), chloro (Cl) or bromo (Br). Particularly preferred, yet non-limiting examples of "halogen" or "halo" are fluoro (F) and chloro (Cl).

The term "cycloalkyl" as used herein refers to a saturated or partly unsaturated monocyclic or bicyclic hydrocarbon group of 3 to 10 ring carbon atoms ("$C_3$-$C_{10}$-cycloalkyl"). In some preferred embodiments, the cycloalkyl group is a saturated monocyclic hydrocarbon group of 3 to 8 ring carbon atoms. "Bicyclic cycloalkyl" refers to cycloalkyl moieties consisting of two saturated carbocycles having two carbon atoms in common, i.e., the bridge separating the two rings is either a single bond or a chain of one or two ring atoms, and to spirocyclic moieties, i.e., the two rings are connected via one common ring atom. Preferably, the cycloalkyl group is a saturated monocyclic hydrocarbon group of 3 to 6 ring carbon atoms, e.g., of 3, 4, 5 or 6 carbon atoms. Some non-limiting examples of cycloalkyl include cyclopropyl, cyclobutyl, cyclopentyl, cyclohexyl and cycloheptyl. A particularly preferred example of cycloalkyl is cyclopropyl.

The terms "heterocyclyl" and "heterocycloalkyl" are used herein interchangeably and refer to a saturated or partly unsaturated mono- or bicyclic, preferably monocyclic ring system of 3 to 10 ring atoms, preferably 3 to 8 ring atoms, wherein 1, 2, or 3 of said ring atoms are heteroatoms selected from N, O and S, the remaining ring atoms being carbon. Preferably, 1 to 2 of said ring atoms are selected from N and O, the remaining ring atoms being carbon. "Bicyclic heterocyclyl" refers to heterocyclic moieties consisting of two cycles having two ring atoms in common, i.e., the bridge separating the two rings is either a single bond or a chain of one or two ring atoms, and to spirocyclic moieties, i.e., the two rings are connected via one common ring atom. Some non-limiting examples of heterocyclyl groups include azetidin-3-yl, azetidin-2-yl, oxetan-3-yl, oxetan-2-yl, 1-piperidyl, 2-piperidyl, 3-piperidyl, 4-piperidyl, 2-oxopyrrolidin-1-yl, 2-oxopyrrolidin-3-yl, 5-oxopyrrolidin-2-yl, 5-oxopyrrolidin-3-yl, 2-oxo-1-piperidyl, 2-oxo-3-piperidyl, 2-oxo-4-piperidyl, 6-oxo-2-piperidyl, 6-oxo-3-piperidyl, morpholino, morpholin-2-yl, morpholin-3-yl, and 2-azaspiro[3.3]heptan-2-yl. Some preferred, yet non-limiting examples of heterocyclyl groups include azetidinyl and 2-azaspiro[3.3]heptan-2-yl.

The term "aryl" refers to a monocyclic, bicyclic, or tricyclic carbocyclic ring system having a total of 6 to 14 ring members ("$C_6$-$C_{14}$-aryl"), preferably, 6 to 12 ring members, and more preferably 6 to 10 ring members, and wherein at least one ring in the system is aromatic. Some non-limiting examples of aryl include phenyl and 9H-fluorenyl (e.g. 9H-fluoren-9-yl). A particularly preferred, yet non-limiting example of aryl is phenyl.

The term "heteroaryl" refers to a mono- or multivalent, monocyclic or bicyclic ring system having a total of 5 to 14 ring members, preferably, 5 to 12 ring members, and more preferably 5 to 10 ring members, wherein at least one ring in the system is aromatic, and at least one ring in the system contains one or more heteroatoms. Preferably, "heteroaryl" refers to a 5-10 membered heteroaryl comprising 1, 2, 3 or 4 heteroatoms independently selected from 0, S and N. Most preferably, "heteroaryl" refers to a 5-10 membered heteroaryl comprising 1 to 2 heteroatoms independently selected from O, S and N. Some preferred, yet non-limiting examples of heteroaryl include thiazolyl (e.g. thiazol-2-yl); oxazolyl (e.g. oxazol-2-yl); 5,6-dihydro-4H-cyclopenta[d]thiazol-2-yl; 1,2,4-oxadiazol-5-yl; pyridyl (e.g. 2-pyridyl); pyrazolyl (e.g. pyrazol-1-yl); imidazolyl (e.g. imidazole-1-yl); benzoxazolyl (e.g. benzoxazol-2-yl) and oxazolo[5,4-c]pyridin-2-yl.

A heterocyclic or heteroaromatic ring can be attached to its pendant group at any heteroatom or carbon atom that results in a stable structure and any of the ring atoms can be optionally substituted.

The term "cyano" refers to a —CN (nitrile) group.

The term "haloalkyl" refers to an alkyl group, wherein at least one of the hydrogen atoms of the alkyl group has been replaced by a halogen atom, preferably fluoro. Preferably, "haloalkyl" refers to an alkyl group wherein 1, 2 or 3 hydrogen atoms of the alkyl group have been replaced by a halogen atom, most preferably fluoro. Particularly preferred, yet non-limiting examples of haloalkyl are trifluoromethyl ($CF_3$) and trifluoroethyl (e.g. 2,2,2-trifluoroethyl).

The term "haloalkoxy" refers to an alkoxy group, wherein at least one of the hydrogen atoms of the alkoxy group has been replaced by a halogen atom, preferably fluoro. Preferably, "haloalkoxy" refers to an alkoxy group wherein 1, 2 or 3 hydrogen atoms of the alkoxy group have been replaced by a halogen atom, most preferably fluoro. A particularly preferred, yet non-limiting example of haloalkoxy is trifluoromethoxy (—$OCF_3$).

The term "aryloxy" refers to an aryl group, as previously defined, attached to the parent molecular moiety via an oxygen atom. A preferred, yet non-limiting example of aryloxy is phenoxy.

The term "cycloalkyloxy" refers to a cycloalkyl group, as previously defined, attached to the parent molecular moiety via an oxygen atom. A preferred, yet non-limiting example of cycloalkyloxy is cyclopropoxy.

The term "heteroaryloxy" refers to a heteroaryl group, as previously defined, attached to the parent molecular moiety via an oxygen atom. A preferred, yet non-limiting example of heteroaryloxy is pyridyloxy (e.g. 2-pyridyloxy, 3-pyridyloxy or 4-pyridyloxy).

The term "heterocyclyloxy" refers to a heterocyclyl group, as previously defined, attached to the parent molecular moiety via an oxygen atom. A preferred, yet non-limiting example of heterocyclyloxy is azetidinyloxy.

The term "pharmaceutically acceptable salt" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are hydrochloride salts.

The term "protective group" (PG) denotes the group which selectively blocks a reactive site in a multifunctional compound such that a chemical reaction can be carried out selectively at another unprotected reactive site in the meaning conventionally associated with it in synthetic chemistry. Protective groups can be removed at the appropriate point. Exemplary protective groups are amino-protective groups, carboxy-protective groups or hydroxy-protective groups. Particular protective groups are the tert-butoxycarbonyl (Boc), benzyloxycarbonyl (Cbz), fluorenylmethoxycarbonyl (Fmoc) and benzyl (Bn). Further particular protective groups are the tert-butoxycarbonyl (Boc) and the fluorenylmethoxycarbonyl (Fmoc). More particular protective group is the tert-butoxycarbonyl (Boc). Exemplary protective groups and their application in organic synthesis are described, for example, in "*Protective Groups in Organic Chemistry*" by T. W. Greene and P. G. M. Wutts, 5th Ed., 2014, John Wiley & Sons, New York.

The term "urea forming reagent" refers to a chemical compound that is able to render a first amine to a species that will react with a second amine, thereby forming an urea derivative. Non-limiting examples of urea forming reagents include bis(trichloromethyl) carbonate, phosgene, trichloromethyl chloroformate, (4-nitrophenyl)carbonate and 1,1'-carbonyldiimidazole. The urea forming reagents described in Sartori, G. et al., *Green Chem.* 2000, 2, 140 are incorporated herein by reference.

The compounds of formula (I) can contain several asymmetric centers and can be present in the form of optically pure enantiomers, mixtures of enantiomers such as, for example, racemates, optically pure diastereioisomers, mixtures of diastereoisomers, diastereoisomeric racemates or mixtures of diastereoisomeric racemates. In a preferred embodiment, the compound of formula (I) according to the invention is a cis-enantiomer of formula (Ia) or (Ib), respectively, as described herein.

According to the Cahn-Ingold-Prelog Convention, the asymmetric carbon atom can be of the "R" or "S" configuration.

The abbreviation "MAGL" refers to the enzyme monoacylglycerol lipase. The terms "MAGL" and "monoacylglycerol lipase" are used herein interchangeably.

The term "treatment" as used herein includes: (1) inhibiting the state, disorder or condition (e.g. arresting, reducing or delaying the development of the disease, or a relapse thereof in case of maintenance treatment, of at least one clinical or subclinical symptom thereof); and/or (2) relieving the condition (i.e., causing regression of the state, disorder or condition or at least one of its clinical or subclinical symptoms). The benefit to a patient to be treated is either statistically significant or at least perceptible to the patient or to the physician. However, it will be appreciated that when a medicament is administered to a patient to treat a disease, the outcome may not always be effective treatment.

The term "prophylaxis" as used herein includes: preventing or delaying the appearance of clinical symptoms of the state, disorder or condition developing in a mammal and especially a human that may be afflicted with or predisposed to the state, disorder or condition but does not yet experience or display clinical or subclinical symptoms of the state, disorder or condition.

The term "neuroinflammation" as used herein relates to acute and chronic inflammation of the nervous tissue, which is the main tissue component of the two parts of the nervous system; the brain and spinal cord of the central nervous system (CNS), and the branching peripheral nerves of the peripheral nervous system (PNS). Chronic neuroinflammation is associated with neurodegenerative diseases such as Alzheimer's disease, Parkinson's disease and multiple sclerosis. Acute neuroinflammation usually follows injury to the central nervous system immediately, e.g., as a result of traumatic brain injury (TBI).

The term "traumatic brain injury" ("TBI", also known as "intracranial injury"), relates to damage to the brain resulting from external mechanical force, such as rapid acceleration or deceleration, impact, blast waves, or penetration by a projectile.

The term "neurodegenerative diseases" relates to diseases that are related to the progressive loss of structure or function of neurons, including death of neurons. Examples of neurodegenerative diseases include, but are not limited to, multiple sclerosis, Alzheimer's disease, Parkinson's disease and amyotrophic lateral sclerosis.

The term "mental disorders" (also called mental illnesses or psychiatric disorders) relates to behavioral or mental patterns that may cause suffering or a poor ability to function in life. Such features may be persistent, relapsing and remitting, or occur as a single episode. Examples of mental disorders include, but are not limited to, anxiety and depression.

The term "pain" relates to an unpleasant sensory and emotional experience associated with actual or potential tissue damage. Examples of pain include, but are not limited to, nociceptive pain, chronic pain (including idiopathic pain), neuropathic pain including chemotherapy induced neuropathy, phantom pain and phsychogenic pain. A particular example of pain is neuropathic pain, which is caused by damage or disease affecting any part of the nervous system involved in bodily feelings (i.e., the somatosensory system). In one embodiment, "pain" is neuropathic pain resulting from amputation or thoracotomy. In one embodiment, "pain" is chemotherapy induced neuropathy.

The term "neurotoxicity" relates to toxicity in the nervous system. It occurs when exposure to natural or artificial toxic substances (neurotoxins) alter the normal activity of the nervous system in such a way as to cause damage to nervous tissue. Examples of neurotoxicity include, but are not limited to, neurotoxicity resulting from exposure to substances used in chemotherapy, radiation treatment, drug therapies, drug abuse, and organ transplants, as well as exposure to heavy metals, certain foods and food additives, pesticides, industrial and/or cleaning solvents, cosmetics, and some naturally occurring substances.

The term "cancer" refers to a disease characterized by the presence of a neoplasm or tumor resulting from abnormal uncontrolled growth of cells (such cells being "cancer cells"). As used herein, the term cancer explicitly includes, but is not limited to, hepatocellular carcinoma, colon carcinogenesis and ovarian cancer.

The term "mammal" as used herein includes both humans and non-humans and includes but is not limited to humans, non-human primates, canines, felines, murines, bovines, equines, and porcines. In a particularly preferred embodiment, the term "mammal" refers to humans.

Compounds of the Invention

In a first aspect, the present invention provides a compound of formula (I)

(I)

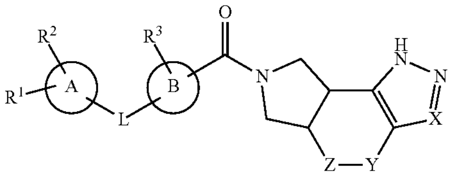

or a pharmaceutically acceptable salt thereof, wherein:

X is CH or N;

Y and Z are $CH_2$ or O, wherein at most one of Y and Z is O;

L is selected from a covalent bond, —$CHR^4$—, —O—, —$OCH_2$—, —$CH_2O$—, —$CH_2OCH_2$—, —$CH_2CH_2$—, —$CF_2CH_2$—, and —$CH_2CF_2$—;

A is selected from $C_6$-$C_{14}$-aryl, 5- to 14-membered heteroaryl, and 3- to 14-membered heterocyclyl;

B is a 4- to 10-membered heterocycle comprising 1-2 nitrogen atoms;

$R^1$ and $R^2$ are independently selected from hydrogen, halogen, $SF_5$, cyano, $C_{1-6}$-alkyl, $C_{1-6}$-alkoxy, halo-$C_{1-6}$-alkyl, halo-$C_{1-6}$-alkoxy, $C_6$-$C_{14}$-aryl, $C_3$-$C_{10}$-cycloalkyl, 5-14-membered heteroaryl, 3- to 14-membered heterocyclyl, $C_6$-$C_{14}$-aryloxy, $C_3$-$C_{10}$-cycloalkyloxy, 3- to 14-membered heterocyclyloxy, and 5-14-membered heteroaryloxy, wherein each of said 3- to 14-membered heterocyclyl, $C_6$-$C_{14}$-aryl, $C_3$-$C_{10}$-cycloalkyl, 5-14-membered heteroaryl, $C_6$-$C_{14}$-aryloxy, $C_3$-$C_{10}$-cycloalkyloxy, and 5-14-membered heteroaryloxy, are optionally substituted with 1-2 substituents selected from halogen, $C_{1-6}$-alkyl, $C_{1-6}$-alkoxy, halo-Cis-alkyl and halo-$C_{1-6}$alkoxy; or $R^1$ and $R^2$, taken together with the atom(s) to which they are attached, form a 3- to 14-membered heterocycle that is optionally substituted with one or more $C_{1-6}$-alkyl;

$R^3$ is selected from hydrogen and $C_{1-6}$-alkyl; and $R^4$ is selected from hydrogen, $C_6$-$C_{14}$-aryl and halo-$C_6$-$C_{14}$-aryl.

In one embodiment, the present invention provides a compound of formula (I) as described herein, or a pharmaceutically acceptable salt thereof, wherein the compound of formula (I) is a compound of formula (IA)

(IA)

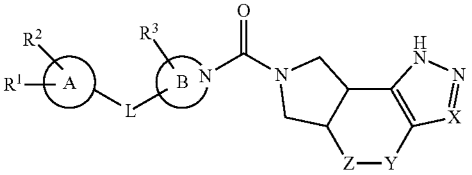

wherein X, Y, Z, A, L, B, and $R^1$ to $R^3$ are as described herein.

In one embodiment, the present invention provides a compound of formula (I) as described herein, or a pharmaceutically acceptable salt thereof, wherein the compound of formula (I) is a compound of formula (IB)

(IB)

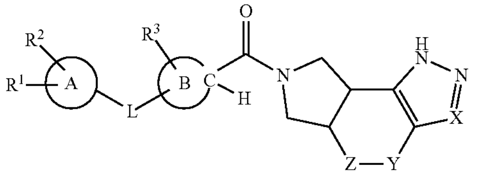

wherein X, Y, Z, A, L, B, and $R^1$ to $R^3$ are as described herein.

In one embodiment, the present invention provides a compound of formula (I) as described herein, or a pharmaceutically acceptable salt thereof, wherein:

X is CH or N;

Y is $CH_2$ or O; and

Z is $CH_2$.

In one embodiment, the present invention provides a compound of formula (I) as described herein, or a pharmaceutically acceptable salt thereof, wherein:

L is selected from a covalent bond, —$CHR^4$—, and —$CH_2O$—;

A is $C_6$-$C_{14}$-aryl;

$R^1$ is selected from halogen, halo-$C_{1-6}$-alkyl, and $C_3$-$C_{10}$-cycloalkyl substituted with halo-$C_{1-6}$-alkyl;

$R^2$ is selected from hydrogen and halogen; and $R^4$ is hydrogen.

In a preferred embodiment, the present invention provides a compound of formula (I) as described herein, or a pharmaceutically acceptable salt thereof, wherein:

L is selected from a covalent bond and —$CH_2O$—;

A is $C_6$-$C_{14}$-aryl;

$R^1$ is selected from halo-$C_{1-6}$-alkyl, and $C_3$-$C_{10}$-cycloalkyl substituted with halo-$C_{1-6}$-alkyl; and $R^2$ is selected from hydrogen and halogen.

In a particularly preferred embodiment, the present invention provides a compound of formula (I) as described herein, or a pharmaceutically acceptable salt thereof, wherein:

L is selected from a covalent bond and —$CH_2O$—;

A is phenyl;

$R^1$ is selected from $CF_3$ and (trifluoromethyl)cyclopropyl; and $R^2$ is selected from hydrogen and fluoro.

In one embodiment, the present invention provides a compound of formula (I) as described herein, or a pharmaceutically acceptable salt thereof, wherein:

B is a 4- to 7-membered heterocycle comprising 1 nitrogen atom; and $R^3$ is hydrogen.

In a preferred embodiment, the present invention provides a compound of formula (I) as described herein, or a pharmaceutically acceptable salt thereof, wherein:

B is azetidinyl; and $R^3$ is hydrogen.

In one embodiment, the present invention provides a compound of formula (I) as described herein, or a pharmaceutically acceptable salt thereof, wherein:

X is CH or N;

Y and Z are $CH_2$ or O, wherein at most one of Y and Z is O;

L is selected from a covalent bond, —$CHR^4$—, and —$CH_2O$—;

A is $C_6$-$C_{14}$-aryl;

B is a 4- to 7-membered heterocycle comprising 1 nitrogen atom;

$R^1$ is selected from halogen, halo-$C_{1-6}$-alkyl, and $C_3$-$C_{10}$-cycloalkyl substituted with halo-$C_{1-6}$-alkyl;

$R^2$ is selected from hydrogen and halogen; and $R^3$ and $R^4$ are both hydrogen.

In a preferred embodiment, the present invention provides a compound of formula (I) as described herein, or a pharmaceutically acceptable salt thereof, wherein:

X is CH or N;

Y is $CH_2$ or O;

Z is $CH_2$;

L is selected from a covalent bond and —$CH_2O$—;

A is $C_6$-$C_{14}$-aryl;

B is a 4- to 7-membered heterocycle comprising 1 nitrogen atom;

$R^1$ is selected from halo-Cis-alkyl, and $C_3$-$C_{10}$-cycloalkyl substituted with halo-$C_{1-6}$-alkyl;

$R^2$ is selected from hydrogen and halogen; and $R^3$ is hydrogen.

In a particularly preferred embodiment, the present invention provides a compound of formula (I) as described herein, or a pharmaceutically acceptable salt thereof, wherein:

X is CH or N;

Y is $CH_2$ or O;

Z is $CH_2$;

L is selected from a covalent bond and —$CH_2O$—;

A is phenyl;

B is azetidinyl;

$R^1$ is selected from $CF_3$ and (trifluoromethyl)cyclopropyl;

$R^2$ is selected from hydrogen and fluoro; and $R^3$ is hydrogen.

In a preferred embodiment, the present invention provides a compound of formula (I) as described herein, or a pharmaceutically acceptable salt thereof, wherein Z is $CH_2$.

In one embodiment, the present invention provides a compound of formula (I) as described herein, or a pharmaceutically acceptable salt thereof, wherein L is selected from a covalent bond, —$CH_2$—, and —$CH_2O$—.

In a preferred embodiment, the present invention provides a compound of formula (I) as described herein, or a pharmaceutically acceptable salt thereof, wherein L is selected from a covalent bond and —$CH_2O$—.

In one embodiment, the present invention provides a compound of formula (I) as described herein, or a pharmaceutically acceptable salt thereof, wherein A is $C_6$-$C_{14}$-aryl.

In a preferred embodiment, the present invention provides a compound of formula (I) as described herein, or a pharmaceutically acceptable salt thereof, wherein A is phenyl.

In one embodiment, the present invention provides a compound of formula (I) as described herein, or a pharmaceutically acceptable salt thereof, wherein B is a 4- to 7-membered heterocycle comprising 1 nitrogen atom.

In a preferred embodiment, the present invention provides a compound of formula (I) as described herein, or a pharmaceutically acceptable salt thereof, wherein B is selected from azetidinyl and 2-azaspiro[3.3]heptan-2-yl.

In a particularly preferred embodiment, the present invention provides a compound of formula (I) as described herein, or a pharmaceutically acceptable salt thereof, wherein B is azetidinyl.

In one embodiment, the present invention provides a compound of formula (I) as described herein, or a pharmaceutically acceptable salt thereof, wherein $R^1$ is selected from halogen, halo-$C_{1-6}$-alkyl, and $C_3$-$C_{10}$-cycloalkyl substituted with halo-$C_{1-6}$-alkyl.

In a preferred embodiment, the present invention provides a compound of formula (I) as described herein, or a pharmaceutically acceptable salt thereof, wherein $R^1$ is selected from halo-$C_{1-6}$-alkyl, and $C_3$-$C_{10}$-cycloalkyl substituted with halo-$C_{1-6}$-alkyl.

In a particularly preferred embodiment, the present invention provides a compound of formula (I) as described herein, or a pharmaceutically acceptable salt thereof, wherein $R^1$ is selected from $CF_3$ and (trifluoromethyl)cyclopropyl.

In one embodiment, the present invention provides a compound of formula (I) as described herein, or a pharmaceutically acceptable salt thereof, wherein $R^2$ is selected from hydrogen and halogen.

In a preferred embodiment, the present invention provides a compound of formula (I) as described herein, or a pharmaceutically acceptable salt thereof, wherein $R^2$ is selected from hydrogen and fluoro.

In a preferred embodiment, the present invention provides a compound of formula (I) as described herein, or a pharmaceutically acceptable salt thereof, wherein $R^3$ is hydrogen. In a preferred embodiment, the present invention provides a compound of formula (I) as described herein, or a pharmaceutically acceptable salt thereof, wherein $R^4$ is hydrogen.

In one embodiment, the present invention provides a compound of formula (I) as described herein, or a pharmaceutically acceptable salt thereof, selected from:

[3-[[2-Fluoro-4-(trifluoromethyl)phenyl]methoxy]azetidin-1-yl]-[rac-(5aR,8aS)-4,5,5a,6,8,8a-hexahydro-1H-pyrrolo[3,4-g]indazol-7-yl]methanone;

[3-[[2-Fluoro-4-(trifluoromethyl)phenyl]methoxy]azetidin-1-yl]-[rac-(1 S,9R)-7-oxa-3,4,11-triazatricyclo[7.3.0.02,6]dodeca-2(6),4-dien-11-yl]methanone;

(−)- or (+)-[(1S,9R)-7-Oxa-3,4,11-triazatricyclo[7.3.0.02,6]dodeca-2(6),4-dien-11-yl]-[3-[4-[1-(trifluoromethyl)cyclopropyl]phenyl]azetidin-1-yl]methanone;

(+)- or (−)-[(1R,9S)-7-Oxa-3,4,11-triazatricyclo[7.3.0.02,6]dodeca-2(6),4-dien-11-yl]-[3-[4-[1-(trifluoromethyl)cyclopropyl]phenyl]azetidin-1-yl]methanone;

(−)- or (+)-[6-[(2,4-Difluorophenyl)methyl]-2-azaspiro[3.3]heptan-2-yl]-[(1S,9R)-7-oxa-3,4,11-triazatricyclo[7.3.0.02,6]dodeca-2(6),4-dien-11-yl]methanone;

(+)- or (−)-[6-[(2,4-Difluorophenyl)methyl]-2-azaspiro[3.3]heptan-2-yl]-[(1R,9S)-7-oxa-3,4,11-triazatricyclo[7.3.0.02,6]dodeca-2(6),4-dien-11-yl]methanone;

(−)- or (+)-[3-[[2-Fluoro-4-(trifluoromethyl)phenyl]methoxy]azetidin-1-yl]-[(5aR,8aS)-4,5,5a, 6,8,8a-hexahydro-1H-pyrrolo[3,4-e]benzotriazol-7-yl]methanone;

(+)- or (−)-[3-[[2-Fluoro-4-(trifluoromethyl)phenyl]methoxy]azetidin-1-yl]-[(5aS,8aR)-4,5,5a,6,8,8a-hexahydro-1H-pyrrolo[3,4-e]benzotriazol-7-yl]methanone;

(−)- or (+)-[3-[[2-Fluoro-4-(trifluoromethyl)phenyl]methoxy]azetidin-1-yl]-[(1S,9R)-8-oxa-3,4,5,11-tetrazatricyclo[7.3.0.02,6]dodeca-2(6),4-dien-11-yl]methanone; and (+)- or (−)-[3-[[2-Fluoro-4-(trifluoromethyl)phenyl]methoxy]azetidin-1-yl]-[(1R,9S)-8-oxa-3,4,5,11-tetrazatricyclo[7.3.0.02,6]dodeca-2(6),4-dien-11-yl]methanone.

In a preferred embodiment, the present invention provides a compound of formula (I) as described herein, or a pharmaceutically acceptable salt thereof, selected from:

(−)- or (+)-[(1S,9R)-7-Oxa-3,4,11-triazatricyclo[7.3.0.02,6]dodeca-2(6),4-dien-11-yl]-[3-[4-[1-(trifluoromethyl)cyclopropyl]phenyl]azetidin-1-yl]methanone; and (−)- or (+)-[3-[[2-Fluoro-4-(trifluoromethyl)phenyl]methoxy]azetidin-1-yl]-[(5aR,8aS)-4,5,5a, 6,8,8a-hexahydro-1H-pyrrolo[3,4-e]benzotriazol-7-yl]methanone.

In a particular embodiment, the present invention provides pharmaceutically acceptable salts of the compounds according to formula (I) as described herein, especially hydrochloride salts. In a further particular embodiment, the present invention provides compounds according to formula (I) as described herein as free bases.

In some embodiments, the compounds of formula (I) are isotopically-labeled by having one or more atoms therein replaced by an atom having a different atomic mass or mass number. Such isotopically-labeled (i.e., radiolabeled) compounds of formula (I) are considered to be within the scope of this disclosure. Examples of isotopes that can be incorporated into the compounds of formula (I) include isotopes of hydrogen, carbon, nitrogen, oxygen, phosphorous, sulfur, fluorine, chlorine, and iodine, such as, but not limited to, $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Certain isotopically-labeled compounds of formula (I), for example, those incorporating a radioactive isotope, are useful in drug and/or substrate tissue distribution studies. The radioactive isotopes tritium, i.e. $^{3}H$, and carbon-14, i.e., $^{14}C$, are particularly useful for this purpose in view of their ease of incorporation and ready means of detection. For example, a compound of formula (I) can be enriched with 1, 2, 5, 10, 25, 50, 75, 90, 95, or 99 percent of a given isotope.

Substitution with heavier isotopes such as deuterium, i.e. $^{2}H$, may afford certain therapeutic advantages resulting from greater metabolic stability, for example, increased in vivo half-life or reduced dosage requirements.

Substitution with positron emitting isotopes, such as $^{11}C$, $^{18}F$, $^{15}O$, and $^{13}N$, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples as set out below using an appropriate isotopically-labeled reagent in place of the non-labeled reagent previously employed.

Processes of Manufacturing

In one aspect, the present invention also provides processes for manufacturing the compounds of formula (I) described herein.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. The substituents and indices used in the following description of the processes have the significance given herein, unless indicated to the contrary.

If one of the starting materials, intermediates or compounds of formula (I) contain one or more functional groups which are not stable or are reactive under the reaction conditions of one or more reaction steps, appropriate protective groups (as described e.g., in "Protective Groups in Organic Chemistry" by T. W. Greene and P. G. M. Wutts, 5th Ed., 2014, John Wiley & Sons, New York) can be introduced before the critical step applying methods well known in the art. Such protective groups can be removed at a later stage of the synthesis using standard methods described in the literature.

If starting materials or intermediates contain stereogenic centers, compounds of formula (I) can be obtained as mixtures of diastereomers or enantiomers, which can be separated by methods well known in the art e.g., chiral HPLC, chiral SFC or chiral crystallization. Racemic compounds can e.g., be separated into their antipodes via diastereomeric salts by crystallization with optically pure acids or by separation of the antipodes by specific chromatographic methods using either a chiral adsorbent or a chiral eluent. It is equally possible to separate starting materials and intermediates containing stereogenic centers to afford diastereomerically/enantiomerically enriched starting materials and intermediates. Using such diastereomerically/enantiomerically enriched starting materials and intermediates in the synthesis of compounds of formula (I) will typically lead to the respective diastereomerically/enantiomerically enriched compounds of formula (I).

A person skilled in the art will acknowledge that in the synthesis of compounds of formula (I)-insofar not desired otherwise—an "orthogonal protection group strategy" will be applied, allowing the cleavage of several protective groups one at a time each without affecting other protective groups in the molecule. The principle of orthogonal protection is well known in the art and has also been described in literature (e.g. Barany, G., Merrifield, R. B., *J. Am. Chem. Soc.* 1977, 99, 7363; Waldmann, H. et al., *Angew. Chem. Int. Ed. Engl.* 1996, 35, 2056).

A person skilled in the art will acknowledge that the sequence of reactions may be varied depending on reactivity and nature of the intermediates.

In more detail, the compounds of formula (I) can be manufactured by the methods given below, by the methods given in the examples or by analogous methods. Appropriate reaction conditions for the individual reaction steps are known to a person skilled in the art. Also, for reaction conditions described in literature affecting the described reactions see for example: "*Comprehensive Organic Transformations: A Guide to Functional Group Preparations*", by Richard C. Larock, 2nd Ed., 1999, John Wiley & Sons, New York. It was found convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux. The time required for the reaction may also vary widely, depending on many factors, notably the reaction temperature and the nature of the reagents. However, a period of from 0.5 hours to several days will usually suffice to yield the described intermediates and compounds. The reaction sequence is not limited to the one displayed in the schemes, however, depending on the starting materials and their respective reactivity, the sequence of reaction steps can be freely altered.

If starting materials or intermediates are not commercially available or their synthesis not described in literature, they can be prepared in analogy to existing procedures for close analogues or as outlined in the experimental section.

The following abbreviations are used in the present text:

AcOH=acetic acid, ACN=acetonitrile, Bn=benzyl, Boc=tert-butyloxycarbonyl, CAS RN=chemical abstracts registration number, Cbz=benzyloxycarbonyl, DAST=(diethylamino)sulfur trifluoride, DBU=1,8-diazabicyclo[5,4,0]undec-7-ene, DEAD=diethyl azodicarboxylate, DIAD=diisopropyl azodicarboxylate, DMAP=4-dimethylaminopyridine, DME=dimethoxyethane, DMEDA=N,N'-dimethylethylenediamine, DMF=N,N-dimethylformamide, DIPEA=N,N-diisopropylethylamine, dppf=1,1 bis(diphenyl phosphino)ferrocene, EDC HCl=N-(3-dimethylaminopropyl)-N'-ethylcarbodiimide hydrochloride, EI=electron impact, ESI=electrospray ionization, EtOAc=ethyl acetate, EtOH=ethanol, h=hour(s), FA=formic acid, HATU=1-[bis(dimethylamino)methylene]-1H-1,2,3-triazolo[4,5-b]pyridinium-3-oxide hexafluorophosphate, HBTU=O-benzotriazole-N,N,N',N'-tetramethyl-uronium-hexafluorophosphate, HOBt=1-hydroxy-1H-benzotriazole, HPLC=high performance liquid chromatography, iPrMgCl=isopropylmagnesium chloride, LG=leaving group, LiHMDS=lithium bis(trimethylsilyl)amide, min=minute(s), mL=milliliter, MPLC=medium pressure liquid chromatography, MS=mass spectrum, nBuLi=n-butyllithium, $T_3P$=propylphosphonic anhydride, PG=protective group, Pd/C=palladium on activated carbon, R=any group, RT=room temperature, SFC=Supercritical Fluid Chromatography, TBME=tert-butyl methyl ether, TEA=triethylamine, TFA=trifluoracetic acid, THE=tetrahydrofuran, Hal=halogen.

Compounds of formula IA wherein X, Y, Z, B, $R^3$, L, A, $R^1$ and $R^2$ are as described herein can be synthesized in analogy to literature procedures and/or as depicted for example in Scheme 1.

Scheme 1

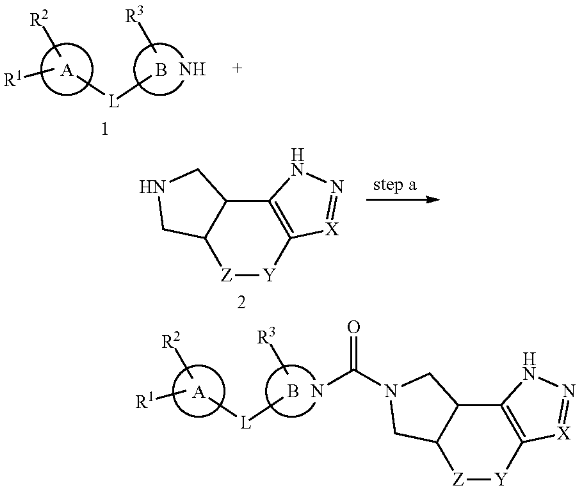

1

2

IA

Accordingly, compounds 1 are reacted with intermediates 2 in the presence of an urea forming reagent such as bis(trichloromethyl) carbonate using a suitable base and solvent such as, e.g. sodium bicarbonate in DCM, to give compounds of formula I (step a). Further urea forming reagents include but are not limited to phosgene, trichloromethyl chloroformate, (4-nitrophenyl)carbonate or 1,1'-carbonyldiimidazole. Reactions of this type and the use of these reagents are widely described in literature (e.g. Sartori, G. et al., *Green Chem.* 2000, 2, 140; Ghosh, A. K. et al., *J. Med. Chem.* 2015, 58, 2895). A person skilled in the art will acknowledge that the order of the addition of the reagents can be important in this type of reactions due to the reactivity and stability of the intermediary formed carbamoyl chlorides, as well as for avoiding formation of undesired symmetrical urea by-products.

Compounds of formula IB wherein X, Y, Z, B, $R^3$, L, A, $R^1$ and $R^2$ are as described herein can be synthesized in analogy to literature procedures and/or as depicted for example in Scheme 2.

Scheme 2

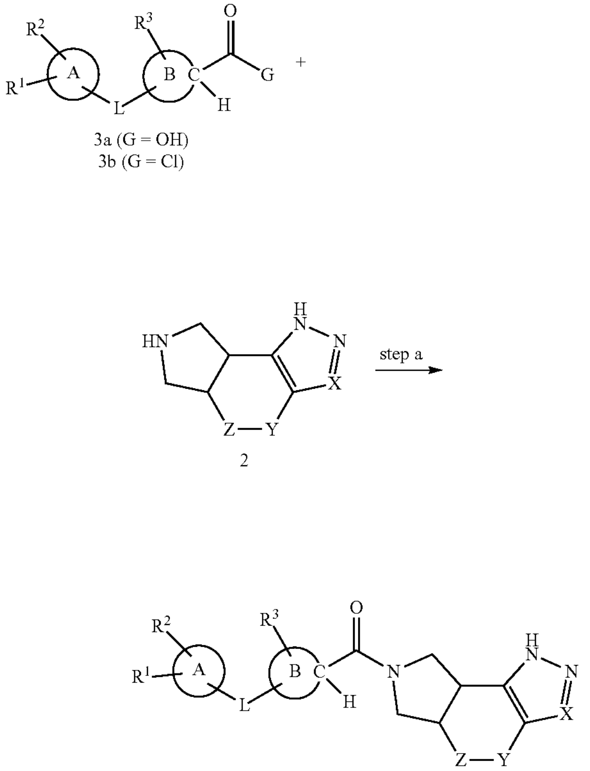

3a (G = OH)
3b (G = Cl)

2

IB

Accordingly, intermediates 2 can be coupled with an activated form of a carboxylic acid 3a (G=OH) or alternatively with carboxylic acid chlorides 3b (G=Cl) to provide compounds IB (step a). Amide couplings of this type are widely described in the literature and can be accomplished by the usage of coupling reagents such as CDI, DCC, HATU, HBTU, HOBT, TBTU, $T_3P$ or Mukaiyama reagent (Mukaiyama, T., Angew. Chem., Int. Ed. Engl. 1979, 18, 707) in a suitable solvent e.g., DMF, DMA, DCM or dioxane, optionally in the presence of a base (e.g. TEA, DIPEA (Huenig's base) or DMAP).

Alternatively, the carboxylic acids 3a can be converted into their acid chlorides 3b by treatment with, e.g. thionyl chloride or oxalyl chloride, neat or optionally in a solvent such as DCM. Subsequent reaction of the acid chloride with intermediates 2 in an appropriate solvent such as DCM or DMF and a base, e.g. TEA, Huenig's base, pyridine, DMAP or lithium bis(trimethylsilyl)amide at temperatures ranging from 0° C. to the reflux temperature of the solvent or solvent mixture yields compounds IB (step a).

In some embodiments tricyclic pyrrolidine intermediates 2 are intermediates of type 2a and 2b, respectively. Intermediates of type 2a in which Q is $CH_2$, and intermediates of type 2b in which Q is O, can be prepared by methods well known by a person skilled in the art and as exemplified by the general synthetic procedure outlined in Scheme 3.

Scheme 3

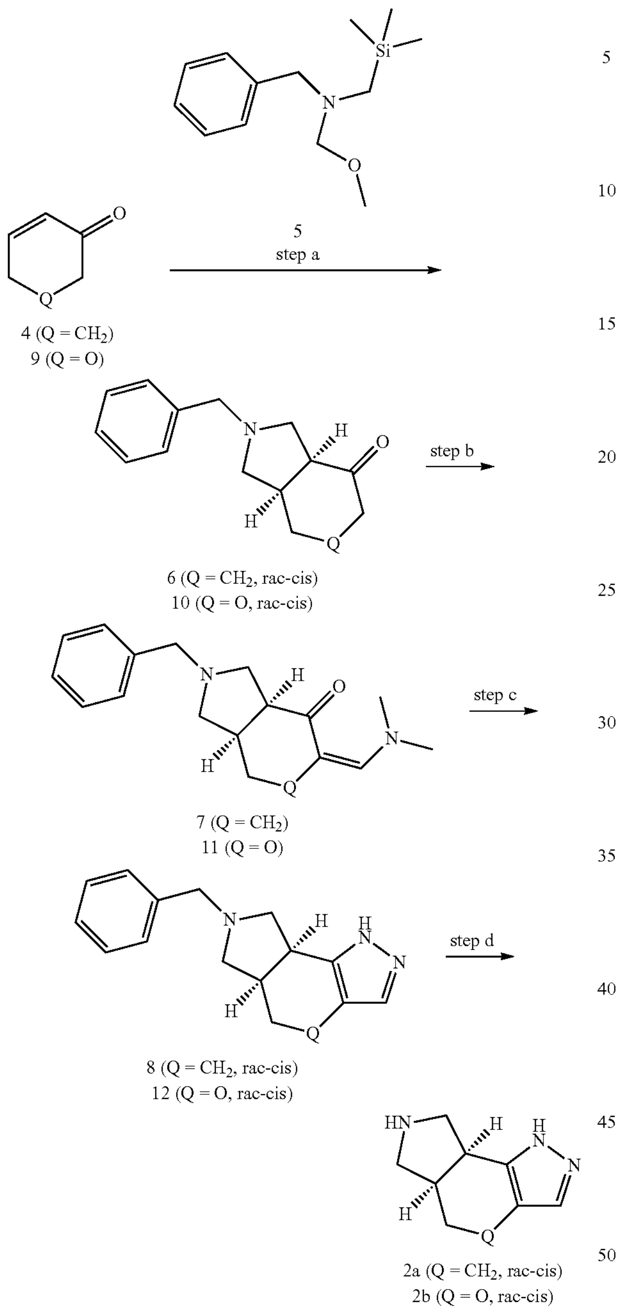

In case intermediates 6 (Q=$CH_2$) or 10 (Q=O) are commercially not available, they can be prepared in analogy to literature procedures, e.g. Kubas, H. et al., *Bioorg. Med. Chem. Lett.* 2013, 23, 6370, by reacting 2-cyclohexen-1-one (4) and 2H-pyran-3(6H)-one (9), respectively, with N-(methoxymethyl)-N-[(trimethylsilyl)methyl]benzenemethanamine in the presence of a suitable acid like TFA in a solvent like DCM (step a).

Intermediates 6 and 10, respectively can then be reacted with 1,1-dimethoxy-N,N-dimethylmethanamine for example in toluene preferable at elevated temperatures to give intermediates 7 and 11, respectively (step b).

Intermediates 7 can be cyclized with hydrazine dihydrochloride in the presence of a suitable base such as NaOH in an appropriate solvent such as MeOH at temperatures ranging from 0° C. up to the boiling point of the solvent to yield intermediates 8 (step c).

The benzyl group in intermediates 8 can be removed by methods known by a person skilled in the art and as described for example in "*Protective Groups in Organic Chemistry*" by T. W. Greene and P. G. M. Wutts, 5th Ed., 2014, John Wiley & Sons, New York, for example by hydrogenation using a suitable catalyst in an appropriate solvent such as palladium on charcoal in MeOH, to furnish intermediates 2a (step d).

Intermediates 11 can be cyclized with hydrazine monohydrate, optionally in the presence of a suitable base such as NaOH, in an appropriate solvent such as EtOH at temperatures ranging from 0° C. up to the boiling point of the solvent to yield intermediates 12 (step c).

The benzyl group in intermediates 12 can be removed as described before for step d to furnish intermediates 2b.

In some embodiments, tricyclic pyrrolidine intermediates 2 are intermediates of type 2c. Intermediates of type 2c can be prepared by methods well known by a person skilled in the art and as exemplified by the general synthetic procedure outlined in Scheme 4.

Scheme 4

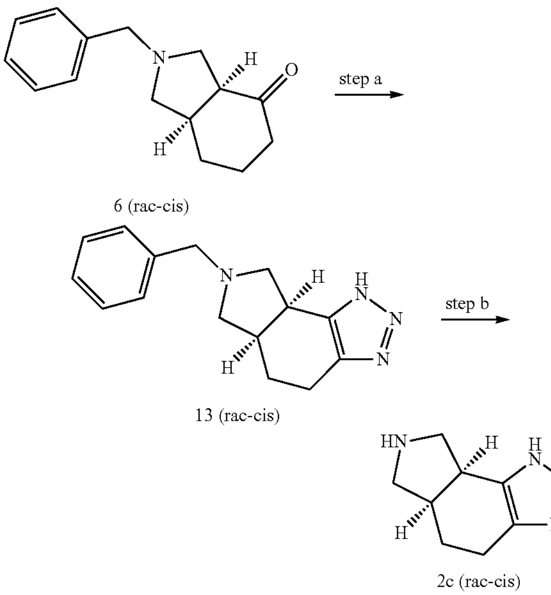

Intermediates 6 can be reacted with 1-azido-4-nitrobenzene in the presence of ammonium acetate in a suitable solvent such as DMF at temperatures ranging from room temperature to the boiling point of the solvent to furnish intermediates 13 (step a).

The benzyl group in intermediates 13 can be removed as described under Scheme 3, step d, to furnish intermediates 2c (step c).

In some embodiments, tricyclic pyrrolidine intermediates 2 are intermediates of type 2d. Intermediates of type 2d can be prepared by methods well known by a person skilled in the art and as exemplified by the general synthetic procedure outlined in Scheme 5.

Scheme 5

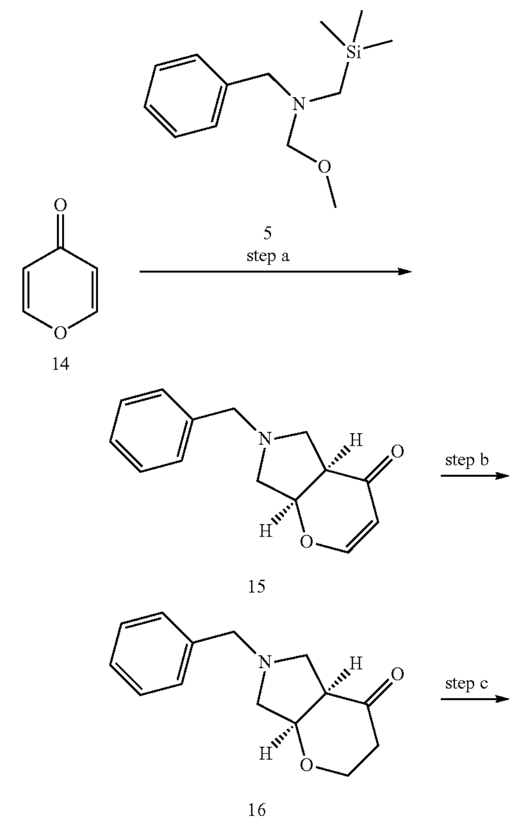

-continued

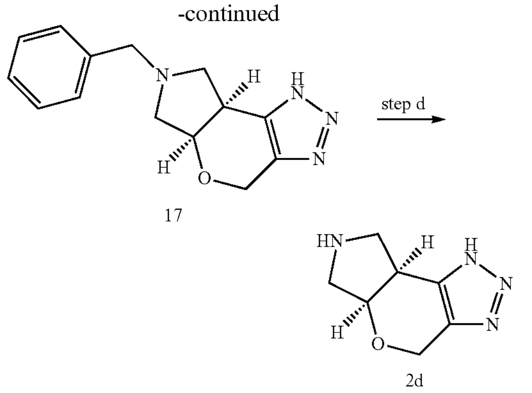

Reaction of 4H-pyran-4-one 14 with N-(methoxymethyl)-N-[(trimethylsilyl)methyl]benzenemethanamine (5) in an appropriate solvent such as ACN, in a temperature range between RT up to the boiling point of the solvent, gives intermediates 15 (step a).

Reduction of the double bond in intermediates 15 applying conditions well known in the art, for example, hydrogenation in the presence of a suitable catalyst such as palladium on charcoal in an appropriate solvent such as EtOAc or MeOH or mixture thereof, yields intermediates 16 (step b).

Reaction of intermediates 16 with 1-azido-4-nitrobenzene in the presence ammonium acetate as described under Scheme 4, step a, furnishes intermediates 17 (step c).

In some embodiments, intermediates 1 are intermediates of type 1a. Intermediates lain which $R^1$, $R^2$, $R^3$, A and B are as described herein can be prepared by a methods known in the art and as exemplified by the general synthetic procedure outlined in Scheme 6.

Scheme 6

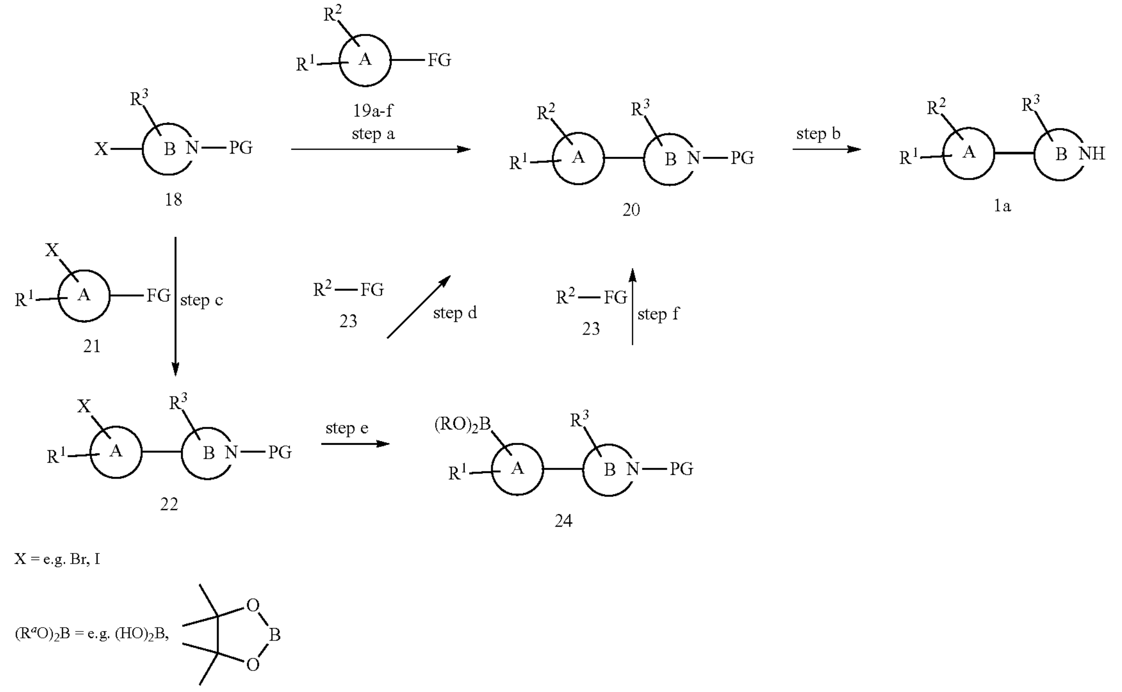

Intermediates 18, either commercially available or prepared by methods known in the art, in which PG signifies a suitable protecting group and X is bromide or iodide can be subjected to cross-coupling reactions such as Negishi, Heck, Stille, Suzuki, Sonogashira or Buchwald-Hartwig coupling reactions with compounds 19, either commercially available or prepared by methods known in the art, in which FG signifies a suitable functional group such as, e.g. chloro, bromo, iodo, —$OSO_2$alkyl (e.g. mesylate (methanesulfonate)), —$OSO_2$fluoroalkyl (e.g. triflate (trifluoromethanesulfonate)) or —$OSO_2$aryl (e.g. tosylate (p-toluenesulfonate)). Reactions of this type are broadly described in literature and well known to persons skilled in the art (step a).

For example, intermediates 18 can be reacted with aryl or heteroaryl boronic acids 19a (FG=$B(OH)_2$) or boronic esters 19b (FG=e.g. 4,4,5,5-tetramethyl-2-phenyl-1,3,2-dioxaborolane (pinacol) ester) either commercially available or prepared using literature procedures as described for example in "*Boronic Acids—Preparation and Applications in Organic Synthesis and Medicine*" by Dennis G. Hall (Ed.), $1^{st}$ Ed., 2005, John Wiley & Sons, New York) using a suitable catalyst (e.g. dichloro[1,1'-bis(diphenylphosphino)-ferrocene]palladium(II) dichloromethane adduct, tetrakis (triphenylphosphine)palladium(0) or palladium(II)acetate with triphenylphosphine) in an appropriate solvent (e.g. dioxane, dimethoxyethane, water, toluene, DMF or mixtures thereof) and a suitable base (e.g. $Na_2CO_3$, $NaHCO_3$, KF, $K_2CO_3$ or TEA) at temperatures between room temperature and the boiling point of the solvent or solvent mixture, to yield intermediates 20 (step a). Suzuki reactions of this type are broadly described in literature (e.g. Suzuki, A., *Pure Appl. Chem.* 1991, 63, 419; Suzuki, A., Miyaura, N., *Chem. Rev.* 1995, 95, 2457; Suzuki, A., *J. Organomet. Chem.* 1999, 576, 147; Polshettiwar, V. et al., *Chem. Sus. Chem.* 2010, 3, 502) and are well known to those skilled in the art. Alternatively, aryl- or heteroaryl-trifluoroborates 19c (FG=BF3) can be used in the cross-coupling reaction applying a palladium catalyst such as, e.g. tetrakis(triphenylphosphine)-palladium(0), palladium(II) acetate or dichloro[1,1'-bis(diphenylphosphino)ferrocene]-palladium(II) dichloromethane adduct in the presence of a suitable base such as cesium carbonate or potassium phosphate in solvents such as toluene, THF, dioxane, water or mixtures thereof, at temperatures between room temperature and the boiling point of the solvent or solvent mixture (step a).

Alternatively, intermediates 18 can be reacted with aryl or heteroaryl stannanes 19d in which FG is $Sn(alkyl)_3$ and alkyl is preferable n-butyl or methyl, using a suitable catalyst and solvent such as, e.g. tetrakis(triphenylphosphine)-palladium (0) in DMF at temperatures between room temperature and the boiling point of the solvent or solvent mixture to provide intermediates 20 (step a). Stille reactions of that type are well known in the art and described in literature, e.g. Farina, V. et al., *Org. React.* 1997, 50, 1; Cordovilla, C. et al., *ACS Catal.* 2015, 5, 3040.

Furthermore, intermediates 18 can be reacted with aryl or heteroarylzinc halides 19e in which FG is ZnHal and Hal preferably bromide or iodide, either commercially available or prepared by literature methods, using an appropriate catalyst and solvent system such as, e.g. [1,1'-bis(diphenylphosphino)ferrocene]dichloropalladium(II) and copper (I)iodide in DMA, or tetrakis(triphenylphosphine)palladium (0) in THF or DMF at temperatures between room temperature and the boiling point of the solvent to provide intermediates 20 (step a). Negishi reactions of that type are well known in the art and also described in literature, e.g. Gavryushin, A. et al., *Org. Lett.*, 2005, 7, 4871; Haas, D. et al., *ACS Catal.* 2016, 6, 1540; Negishi, E. I., *Acc. Chem. Res.* 1982, 15, 340. Alternatively, intermediates 20 may be prepared by first converting intermediates 18 in which X is for example iodide into the corresponding zinc species by applying literature methods (e.g. reaction of 18 with Zn powder in the presence of chlorotrimethylsilane and 1,2-dibromoethane in a suitable solvent such as DMA) and subsequent coupling of the zinc species with aryl- or heteroarylbromides- or iodides under the conditions mentioned before.

Alternatively, intermediates 18 in which X is preferably bromide can be subjected to a cross-electrophile coupling with aryl- or heteroarylbromides 19f in which FG signifies bromide under irradiation with a 420 nm blue light lamp using an appropriate photo catalyst such as $[Ir\{dF(CF_3)ppy\}_2(dtbpy)]PF_6$ ([4,4'-bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate), a Nickel catalyst like $NiCl_2$ glyme (dichloro(dimethoxyethane)nickel), 4,4'-di-tert-butyl-2,2'-dipyridyl and tris(trimethylsilyl)silane, in the presence of a suitable base such as anhydrous sodium carbonate in a solvent like DME. Reactions of this type are described in literature, e.g. Zhang, P. et al., *J. Am. Chem. Soc.* 2016, 138, 8084; Prier, C. K. et al., *Chem. Rev.* 2013, 113, 5322 (step a).

Furthermore, intermediates 18 in which LG is preferably iodine can be subjected to Suzuki-Miyaura cross coupling reactions with arylboronic acids 21 (FG=$B(OH)_2$) using a suitable Nickel catalyst such as nickel(II) iodide in the presence of rac-(1R,2R)-2-aminocyclohexan-1-ol and a suitable base such as sodium bis(trimethylsilyl)amide in an appropriate solvent like iPrOH, dioxane, THE or DME, preferably iPrOH, at temperatures between room temperature and the boiling point of the solvent, optionally applying microwave heating, to yield intermediates 22. Reactions of this type are described in literature, e.g. Dequirez, G. et al., *ChemistrySelect* 2017, 2, 8841 (step c).

Intermediates 22 can be reacted with compounds $R^2$-FG 23 applying one of the cross-coupling methods described before to provide intermediates 20 (step d).

The bromo or iodo substituent in intermediates 22 can be converted into a boronic acid or boronic ester (e.g. pinacol ester) according to methods described in the literature or as outlined under step a, to yield intermediates 24 (step e).

Intermediates 24 can be converted to intermediates 20 for example using a Suzuki coupling reaction with compounds $R^2$-FG 23 in which FG is for example bromine or iodine applying the conditions described under step a (step 0.

Removal of the protective group from intermediates 20 applying methods well known in the art and as described, e.g. furnishes intermediates 1a (step b).

In some embodiments, intermediates 1 are intermediates of type 1b. Intermediates 1b in which $R^1$, $R^2$, $R^3$, $R^4$, A and B are as described herein can be prepared by a variety of conditions, which may be exemplified by the general synthetic procedure outlined in Scheme 7.

Scheme 7

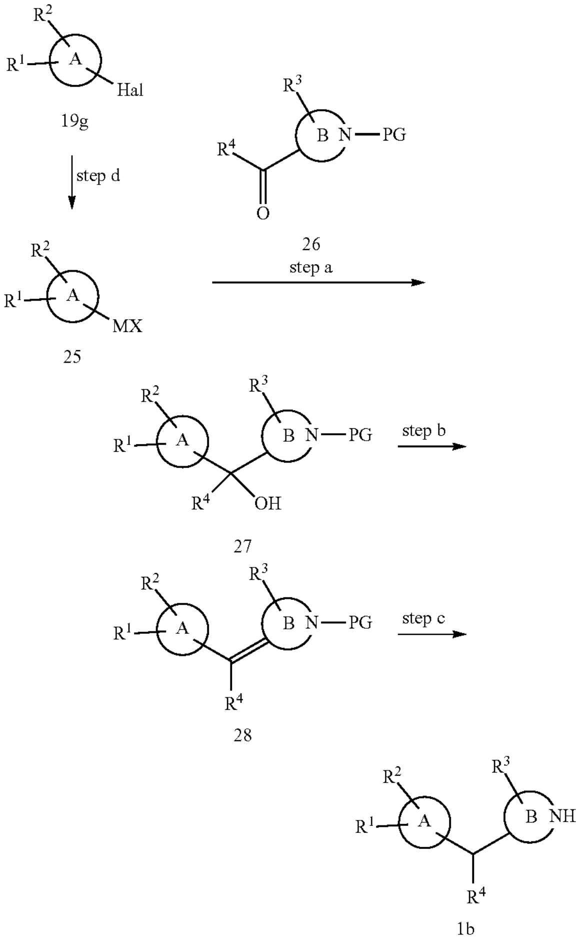

Addition of an organometallic compound of type 25 in which MX is for example Li or MgCl, MgBr or MgI to intermediates 26 in which PG is a suitable protective group, e.g. a Boc group, provides intermediates 27 (step a). Reactions of this type are well known in the art and described in literature (Walsh, D. A. et al., *J. Med. Chem.* 1989, 32, 105; He, S. et al., *J. Med. Chem.* 2014, 57, 1543; Senter, T. et al., *Bioorg. Med. Chem. Lett.* 2015, 25, 2720). In case compounds 25 in which MX=MgHal with Hal being Cl, Br or I (Grignard reagents) are commercially not available they may be prepared for example by reaction of the corresponding aryl or heteroaryl halides 19 g with magnesium in a suitable solvent such as THF, optionally in the presence of catalytic amounts of iodine at temperatures ranging from 0° C. to the boiling point of the solvent (step d). Alternatively, a lithium halogen exchange reaction can be performed with aryl or heteroaryl halides 19 g using a solution of LiHMDS or nBuLi, preferably nBuLi in a solvent like THF, diethyl ether, n-pentane, n-hexane or mixtures thereof, preferably THF and in a temperature range between −20° C. and −78° C., preferably at −78° C., to generate the corresponding lithiated aryl or heteroaryl intermediate (M=Li). Nucleophilic addition of the in situ prepared lithiated aryl or heteroaryl intermediate to ketones of type 26 in which PG is a suitable protecting group such as a Boc group in a solvent such as THF and preferably at a temperature of −78° C. gives the corresponding tertiary alcohols 27 (step a).

Subsequent elimination of the tertiary hydroxy group in intermediates 27, optionally with concomitant removal of an acid labile protective group (e.g. a Boc protective group) using acidic conditions such as 4 M HCl in dioxane in a solvent like MeOH, or, preferably, TFA in DCM, yields the corresponding olefinic intermediates 28 (step b). Heterogeneous catalytic hydrogenation of olefins 28 using a catalyst such as $Pd(OH)_2$ or Pd/C in a solvent like THF, MeOH, EtOH, EtOAc or a mixture thereof, preferably Pd/C in THF under e.g., atmospheric pressure of hydrogen, affords intermediates of type 1b (step c).

Intermediates 26 are commercially available and/or can be prepared in analogy to methods described in literature, e.g. Ashton, K. S. et al., *Bioorg. Med. Chem. Lett.* 2011, 21, 5191; WO2012/155199; WO2016/180536; Hutchings, K. M. et al., *Bioorg. Med. Chem. Lett.* 2008, 18, 5087; WO2007/117557; Zhang, X., MacMillan, D. W. C., *J. Am. Chem. Soc.* 2017, 139, 11353; Liu, F. et al., *J. Med. Chem.* 2017, 60, 5507.

In some embodiments, intermediates 1 are intermediates of type 1c. Intermediates 1c in which $R^1$, $R^2$, $R^3$, A and B are as described herein can be prepared by a methods well known in the art and as exemplified by the general synthetic procedure outlined in Scheme 8.

Scheme 8

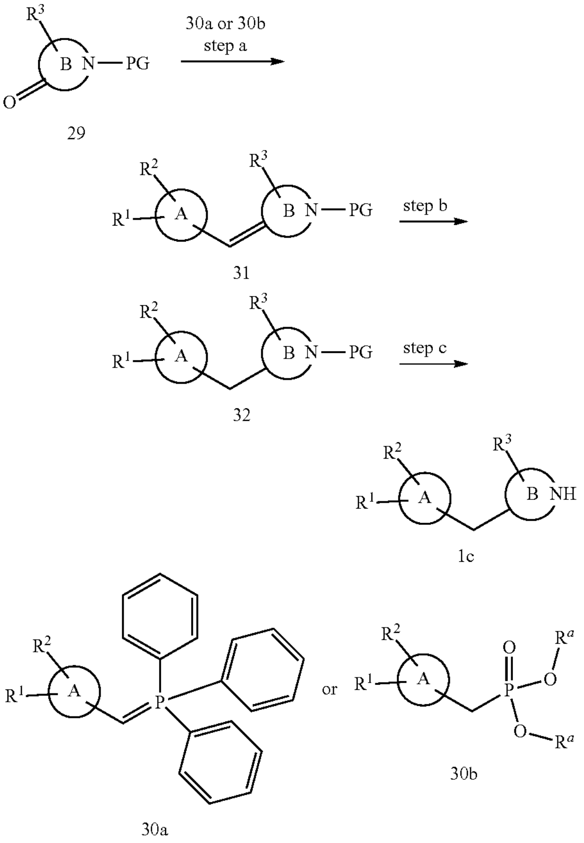

Ketones 29 in which PG is a suitable protective group, either commercially available or prepared by methods known in the art, can be subjected for example to a Wittig reaction with alkylidene triphenylphosphoranes of type 30a in a suitable solvent such as, e.g. THF, Methyl-THF or DMSO to give intermediates 31 (step a). Phosphoranes 30a can be formed by treating the corresponding phosphonium salts with a suitable base such as nBuLi, NaH, or KOtBu in a suitable solvent such as THF, dioxane or Methyl-THF and may be isolated or used in situ. Phosphonium salts in turn are readily available from an aryl/heteroaryl/heterocyclic-substituted alkylhalide (with halide being Cl, Br and I) and triphenylphosphine in a suitable solvent such as toluene. Heating may be applied to accelerate the reaction or drive the reaction to completion (e.g. “Preparation, Properties and Reactions of Phosphonium Salts” by H. J. Cristau, F. Plenat in *The Chemistry of Organophosphorus Compounds: Phosphonium Salts, Ylides And Phosphoranes* (Patai’s Chemistry of Functional Groups), Vol. 3, Frank R. Hartley (Ed.), Series Editor: Prof. Saul Patai, John Wiley & Sons, New York).

Alternatively, intermediates 31 can be obtained using a Horner-Wadsworth-Emmons (HWE) reaction using ketones 29 and phosphonates 30b, wherein Ra is alkyl, for example methyl or ethyl. Phosphonates 30b are in situ α-metalated palladium on charcoal in an appropriate solvent or solvent mixture such as EtOAc, MeOH or AcOH yields compounds 32 (step b).

Removal of the protective group from intermediates 32 applying methods known in the art (e.g. a Boc group using TFA in DCM or 4 M HCl in dioxane at temperatures between 0° C. and room temperature, a Cbz group using hydrogen in the presence of a suitable catalyst such as Pd or $Pd(OH)_2$ on charcoal in a suitable solvent such as MeOH, EtOH, EtOAc or mixtures thereof and as described for example in “*Protective Groups in Organic Chemistry*” by T. W. Greene and P. G. M. Wutts, 5th Ed., 2014, John Wiley & Sons, New York), furnishes intermediates 1c (step c).

In some embodiments, intermediates 1 are intermediates of type 1d. Intermediates 1d in which $R^1$, $R^2$, $R^3$, A and B are as described herein can be prepared by a methods well known in the art and as exemplified by the general synthetic procedure outlined in Scheme 9.

Scheme 9

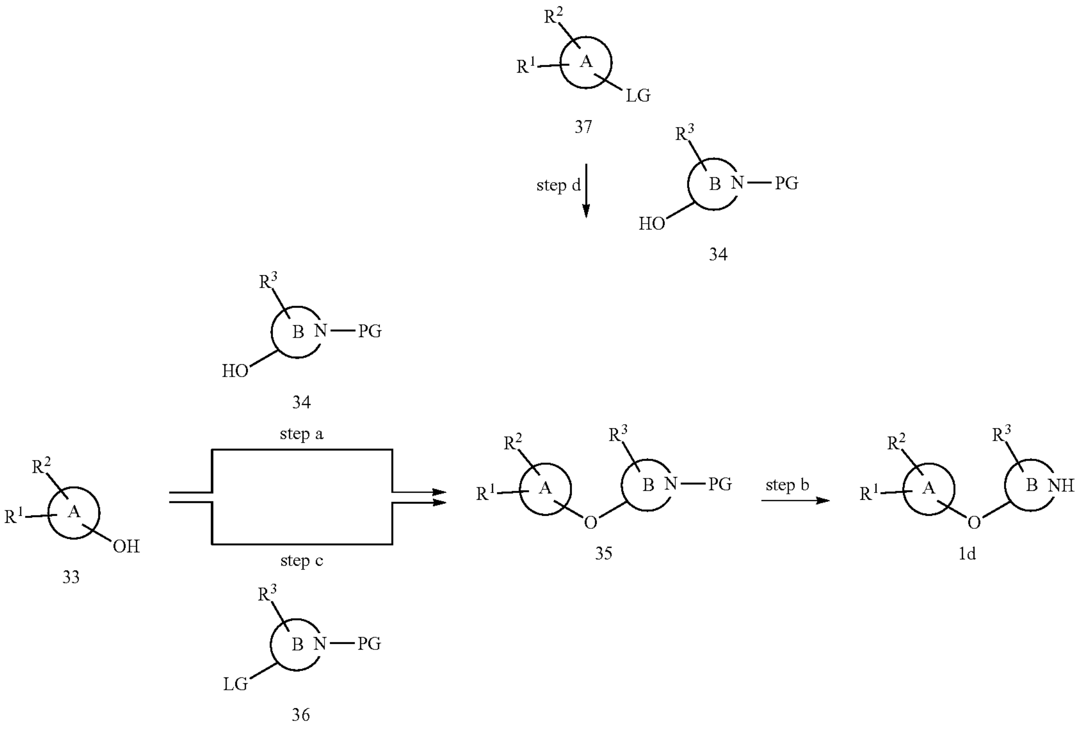

using a suitable base and solvent such as NaH, nBuLi or KOtBu in THE (step a). Phosphonates 30b are readily prepared using for example the Arbuzov reaction by alkylation of an aryl/heteroaryl/heterocyclic halide (with halide being Cl, Br and I) with commercially available trialkyl phosphite (e.g. Brill, T. B., Landon, S. J., *Chem. Rev.* 1984, 84, 577).

Olefination reactions of both types are broadly described in literature (e.g. Bisceglia, J. A., Orelli, L. R., Curr. Org. Chem. 2015, 19, 744; Maryanoff, B. E., Reitz, A. B., Chem. Rev. 1989, 89, 863; Wadsworth Jr., W. S., *Org. React.* 1977, 25, 73; Nicolaou, K. C., Hartner, M. W., Gunzner, J. L., Nadin, A., *Liebigs Ann./Recueil* 1997, 1283; Stec, W. J., *Acc. Chem. Res.* 1983, 16, 411).

Reduction of the double bond in intermediates 31 using, e.g. hydrogen in the presence of a suitable catalyst such as Alcohols of type 33 can be subjected to a Mitsunobu reaction with intermediates 34 in which PG is a suitable protective group such as a Cbz, Boc or Bn, using an appropriate phosphine such as triphenylphosphine and a dialkyl azodicarboxylate such as DEAD or DIAD in a suitable solvent such as THE to give intermediates 19 (step a). Mitsunobu reactions of that type are broadly described in literature (e.g. Fletcher, S., *Org. Chem. Front.* 2015, 2, 739; Kumara Swamy, K. C., et al., *Chem. Rev.* 2009, 109, 2551).

Removal of the protective group from intermediates 35 applying literature methods and as described for example under Scheme 8, step c, furnishes intermediates 1D (step b).

Alternatively, intermediates 35 may be prepared from alcohols 33 that can be alkylated with compounds 36 in which LG is a suitable leaving group such as chlorine, bromine, iodine, $OSO_2$alkyl (e.g. methanesulfonate), $OSO_2$fluoroalkyl (e.g. trifluoromethanesulfonate) or $OSO_2$aryl (e.g. p-toluenesulfonate using a suitable base in an appropriate solvent (e.g. sodium hydride in DMF) at temperatures between 0° C. and the boiling temperature of the solvent (step c).

Furthermore, intermediates 35 may be synthesized via alkylation of alcohols of type 34 with compounds 37 under the conditions described under step c.

In some embodiments, intermediates 1 are intermediates of type 1e. Intermediates 1e in which $R^1$, $R^2$, $R^3$, A and B are as described herein can be prepared by a variety of conditions, which may be exemplified by the general synthetic procedure outlined in Scheme 10.

Scheme 10

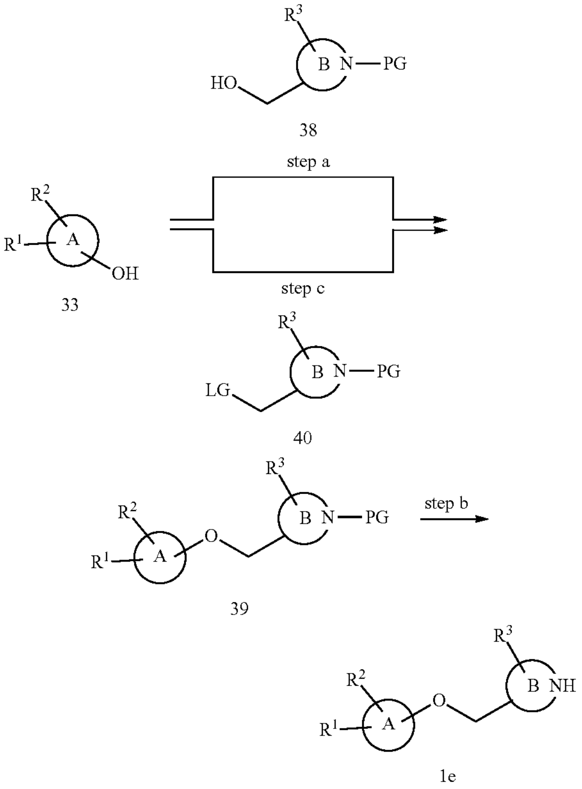

PG = Protecting group
LG = Leaving group

Alcohols of type 33 can be subjected to a Mitsunobu reaction with intermediates 38 in which PG is a suitable protective group such as a Cbz, Boc or Bn, using an appropriate phosphine such as triphenylphosphine and a dialkyl azodicarboxylate such as DEAD or DIAD in a suitable solvent such as THE to give intermediates 39 (step a). Mitsunobu reactions of that type are broadly described in literature (e.g. Fletcher, S., *Org. Chem. Front.* 2015, 2, 739; Kumara Swamy, K. C., et al., *Chem. Rev.* 2009, 109, 2551).

Removal of the protective group from intermediates 39 applying literature methods and as described for example under Scheme 8, step c, furnishes intermediates 1e (step b).

Alternatively, intermediates 39 may be prepared from alcohols 33 that can be alkylated with compounds 40 in which LG is a suitable leaving group such as chlorine, bromine, iodine, $OSO_2$alkyl (e.g. methanesulfonate), $OSO_2$fluoroalkyl (e.g. trifluoromethanesulfonate) or $OSO_2$aryl (e.g. p-toluenesulfonate) using a suitable base such as $Cs_2CO_3$, Huenig's base or NaH, in an appropriate solvent, such as DMF at temperatures between 0° C. and the boiling temperature of the solvent (step c).

Reacting intermediates 1e with intermediates 2, for example using the conditions described under Scheme 1, step a, affords compounds of type IC, wherein $R^1$, $R^2$, $R^3$, A, B, X, Y and Z are as defined herein.

IC

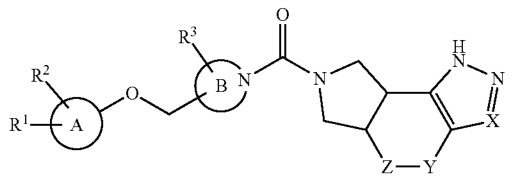

Alternatively, compounds of type IC may be prepared according to Scheme 11.

Scheme 11

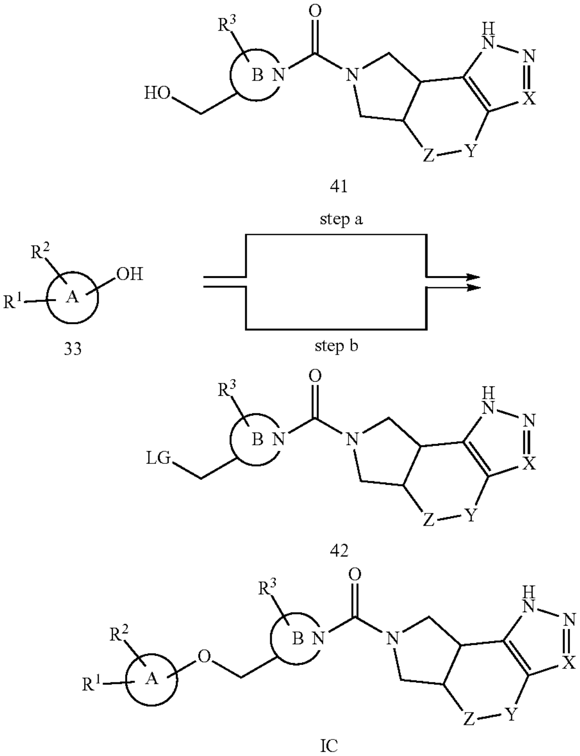

Alcohols of type 33 can be subjected to a Mitsunobu reaction with intermediates 41, using an appropriate phosphine such as triphenylphosphine and a dialkyl azodicarboxylate such as DEAD or DIAD in a suitable solvent such as THE to give compounds ID (step a). Mitsunobu reactions of that type are broadly described in literature (e.g. Fletcher, S., *Org. Chem. Front.* 2015, 2, 739; Kumara Swamy, K. C., et al., *Chem. Rev.* 2009, 109, 2551).

Alternatively, compounds IC may be directly prepared from alcohols 33 that can be alkylated with compounds 42 in which LG is a suitable leaving group such as chlorine, bromine, iodine, $OSO_2$alkyl (e.g. methanesulfonate), $OSO_2$fluoroalkyl (e.g. trifluoromethanesulfonate) or $OSO_2$aryl (e.g. p-toluenesulfonate) using a suitable base such as $Cs_2CO_3$, Huenig's base or NaH, in an appropriate solvent, such as DMF at temperatures between 0° C. and the boiling temperature of the solvent (step b).

In some embodiments, intermediates 1 are intermediates of type 1f Intermediates 1f in which $R^1$, $R^2$, $R^3$, A and B are as described herein can be prepared by a methods known in the art and as exemplified by the general synthetic procedure outlined in Scheme 12.

Scheme 12

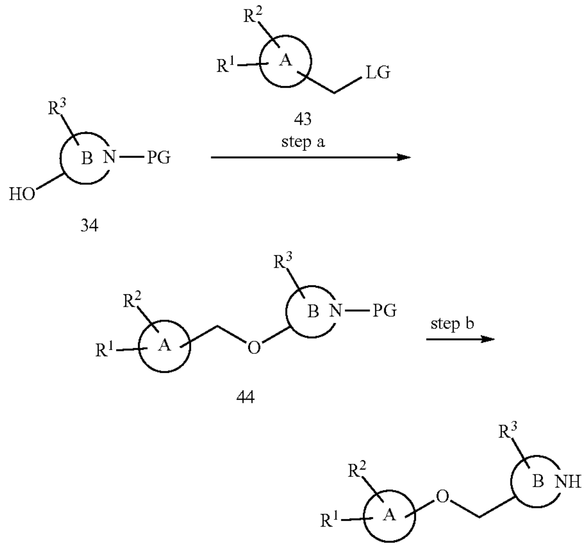

43
34
44
1f

Intermediates 44 may be prepared from alcohols 34, either commercially available or prepared by methods known by a person skilled in the art and in which PG is a suitable protective group such as a Cbz, Boc or Bn, by alkylation with compounds 43 in which LG is a suitable leaving group such as chlorine, bromine, iodine, $OSO_2$alkyl (e.g. methanesulfonate), $OSO_2$fluoroalkyl (e.g. trifluoromethanesulfonate) or $OSO_2$aryl (e.g. p-toluenesulfonate) using a suitable base, such as sodium hydride, Huenig's base or potassium tert-butoxide, in an appropriate solvent (e.g. in DMF or THF) at temperatures between 0° C. and the boiling temperature of the solvent (step a).

Removal of the protective group from intermediates 44 applying methods known in the art (e.g. a Boc group using TFA in DCM at temperatures between 0° C. and room temperature, a Cbz group using hydrogen in the presence of a suitable catalyst such as Pd or $Pd(OH)_2$ on charcoal in a suitable solvent such as MeOH, EtOH, EtOAc or mixtures therefore and as described for example in "*Protective Groups in Organic Chemistry*" by T. W. Greene and P. G. M. Wutts, 5th Ed., 2014, John Wiley & Sons, New York), furnishes intermediates 1f (step b).

In some embodiments, intermediates 1 are intermediates of type 1 g. Intermediates 1 g in which $R^1$, $R^2$, $R^3$, A and B are as described herein can be prepared by a variety of conditions, which may be exemplified by the general synthetic procedure outlined in Scheme 13.

Scheme 13

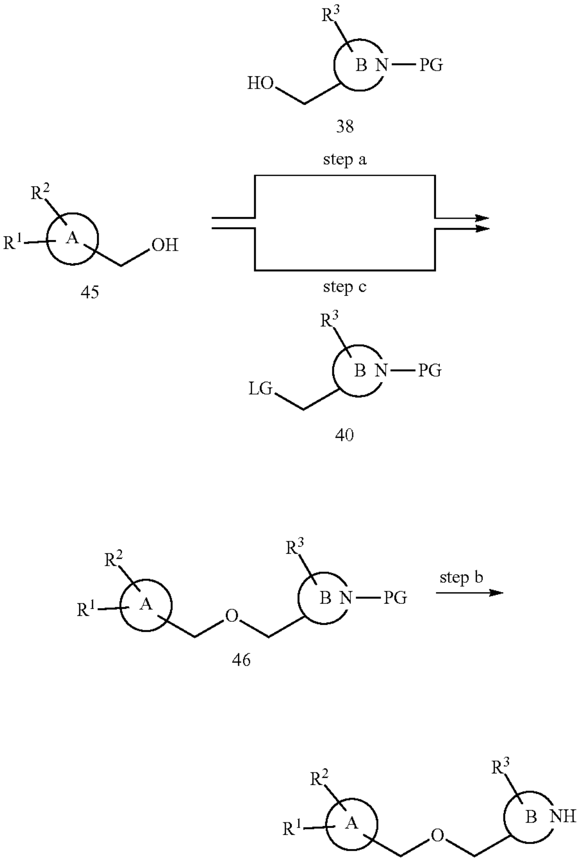

38
45
40
46
1f

Alcohols of type 45 can be subjected to a Mitsunobu reaction with intermediates 38 in which PG is a suitable protective group such as a Cbz, Boc or Bn, using an appropriate phosphine such as triphenylphosphine and a dialkyl azodicarboxylate such as DEAD or DIAD in a suitable solvent such as THE to give intermediates 46 (step a). Mitsunobu reactions of that type are broadly described in literature (e.g. Fletcher, S., *Org. Chem. Front.* 2015, 2, 739; Kumara Swamy, K. C., et al., *Chem. Rev.* 2009, 109, 2551).

Removal of the protective group from intermediates 46 applying literature methods and as described for example under Scheme 4, step c, furnishes intermediates 1f (step b).

Alternatively, intermediates 46 may be prepared from alcohols 45 that can be alkylated with compounds 40 in which LG is a suitable leaving group such as chlorine, bromine, iodine, $OSO_2$alkyl (e.g. methanesulfonate), $OSO_2$fluoroalkyl (e.g. trifluoromethanesulfonate) or $OSO_2$aryl (e.g. p-toluenesulfonate) using a suitable base such as $Cs_2CO_3$, Huenig's base or NaH, in an appropriate solvent, such as DMF at temperatures between 0° C. and the boiling temperature of the solvent (step c).

In some embodiments, intermediates 1 are intermediates of type 1 g and 1 h, respectively. Intermediates of type 1 g and 1 h in which $R^1$, $R^2$, $R^3$, A and B are as described herein can be prepared by methods well known by a person skilled in the art and as exemplified by the general synthetic procedures outlined in Scheme 14.

Scheme 14

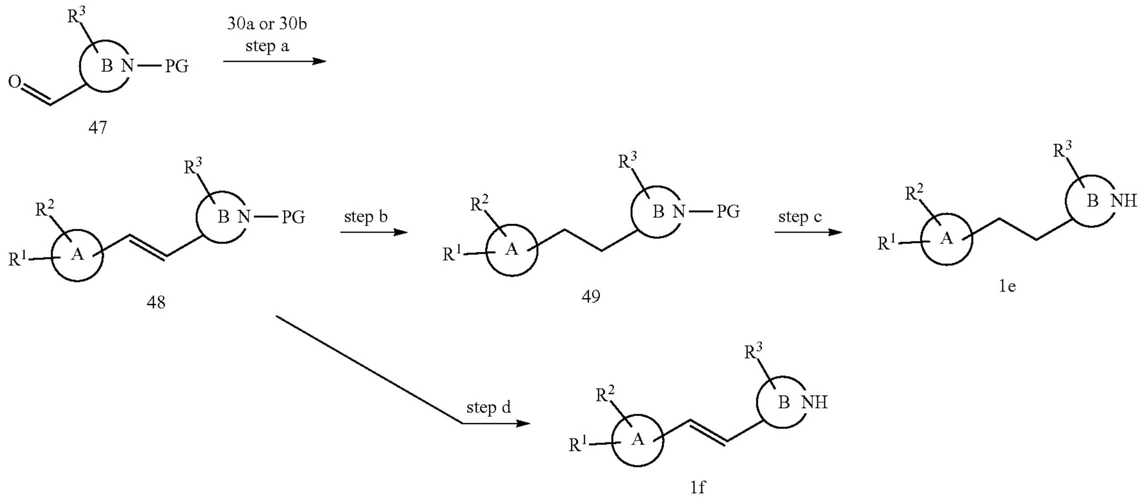

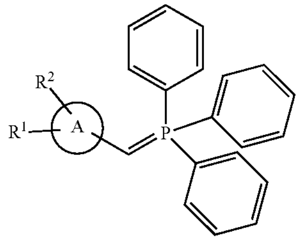

or

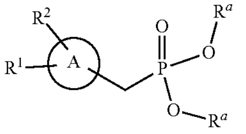

30b

30a $R^a$ = e.g. Me, Et

Aldehydes 47, either commercially available or prepared by methods known in the art, can be subjected to a Wittig reaction or Horner-Wadsworth-Emmons (HWE) reaction using alkylidene triphenylphosphoranes of type 30a and phosphonates 30b, respectively, using for example the conditions described under Scheme 8, step a, to give intermediates 48 (step a).

Reduction of the double bond in intermediates 48 applying literature conditions or the conditions described under Scheme 5, step b or Scheme 7, step c, yields compounds 49 (step b).

Removal of the protective group from intermediates 49 applying methods known in the art and as outlined under Scheme 8, step c, furnishes intermediates 1e (step c).

Removal of the protective group from intermediates 48 applying methods known in the art and as outlined under Scheme 8, step c, furnishes intermediates 1f (step d).

In another embodiment, intermediates 1 are intermediates of type 1 g. Intermediates of type 1 g in which $R^1$, $R^2$, $R^3$, A and B are as described herein, can be prepared by methods well known in the art and as exemplified by the general synthetic procedures outlined in Scheme 15.

Scheme 15

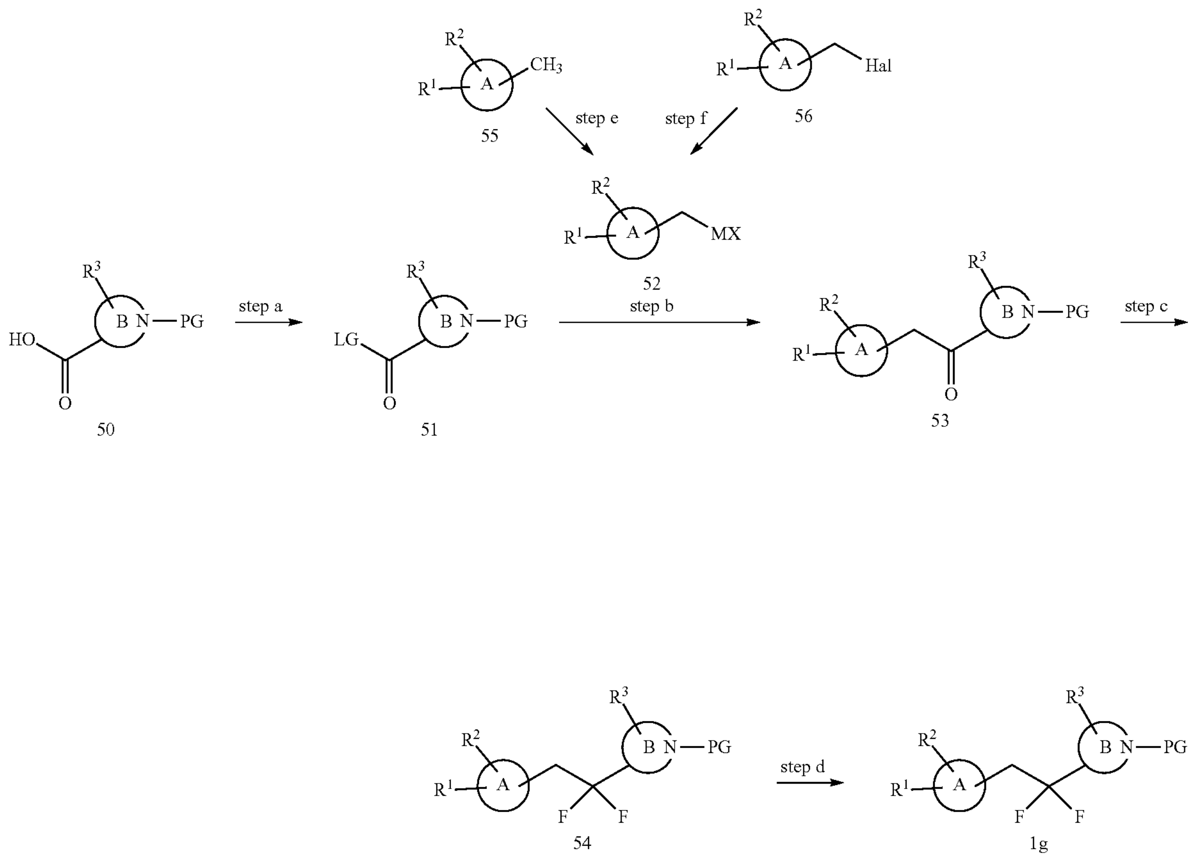

55 56 52 50 51 53 54 1g

The carboxylic acid functionality in derivatives 50 in which PG signifies a suitable protecting group such as, e.g. a Boc, Cbz or Bn protecting group, either commercially available or prepared by methods known in the art, can be converted into an acid chloride (LG=Cl) or Weinreb amide (LG=NMeOMe) by applying methods broadly described in literature to give intermediates 51 (step a).

Intermediates 51 can be reacted with compounds of type 52, either commercially available or synthesized by methods known in the art and as described below to yield intermediates 53 (step b).

Compounds 53 can be further converted into compounds 54 by a deoxyfluorination reaction using a suitable fluorinating agent such as DAST, Deoxo-Fluor (bis(2-methoxyethyl)aminosulfur trifluoride) or aminodifluorosulfinium tetrafluoroborates (XtalFluor-E®, XtalFluor-M® in the presence of, e.g. triethylamine trihydrofluoride and TEA or DBU) in a suitable solvent such as DCM or ACN (step c).

Removal of the protective group from intermediates 54 applying literature methods and as described for example under Scheme 8, step c, furnishes intermediates 1 g (step d).

If compounds 52 are commercially not available, they can be prepared in analogy to literature methods. For example, deprotonation of a reactive methyl group in optionally substituted heterocycles 55 using an appropriate base such nBuLi or LiHMDS in a suitable solvent, e.g. THF, hexane or mixtures thereof, at temperatures ranging from −78° C. to room temperature, gives intermediates 52 in which MX=Li (step e).

Compounds 52 in which MX=MgHal with Hal being Cl, Br or I (Grignard reagents) may be prepared by reaction of the corresponding substituted benzyl halides 56 with magnesium in a suitable solvent such as THF, optionally in the presence of catalytic amounts of iodine at temperatures ranging from 0° C. to the boiling point of the solvent (step f).

In another embodiment, intermediates 1 are intermediates of type 1 h. Intermediates of type 1 h in which $R^1$, $R^2$, $R^3$, A and B are as described herein, can be prepared by methods well known in the art and as exemplified by the general synthetic procedures outlined in Scheme 16.

Scheme 16

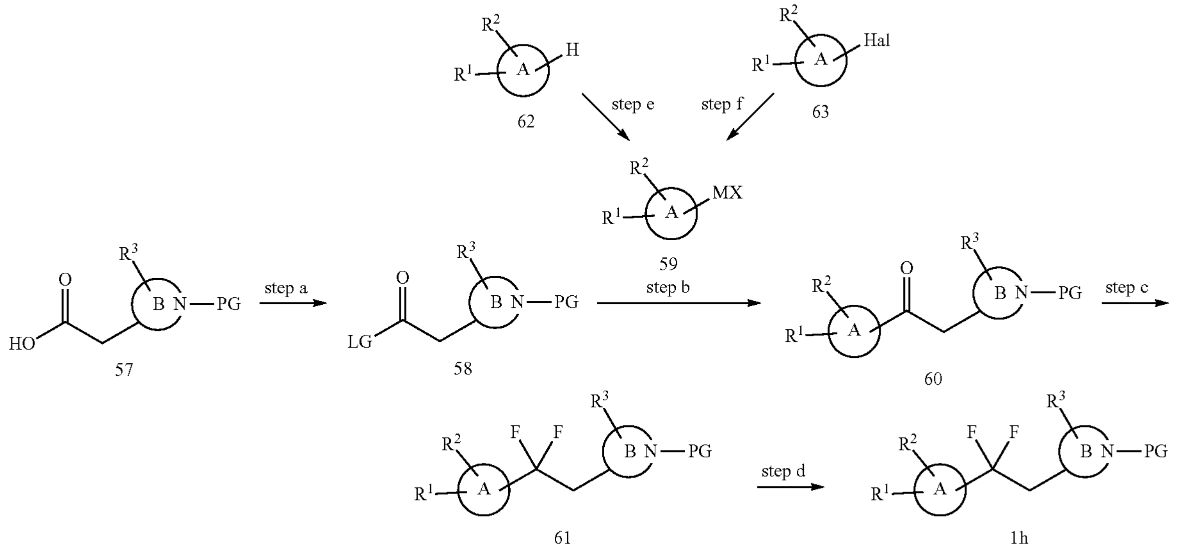

62, 63, 59, 57, 58, 60, 61, 1h

The carboxylic acid functionality in intermediates 57, either commercially available or prepared by methods known in the art, in which PG signifies a suitable protecting group such as, e.g. a Boc, Cbz or Bn protecting group, can be converted for example into an acid chloride (LG=Cl) or Weinreb amide (LG=NMeOMe) by applying methods broadly described in literature to give intermediates 58 (step a).

Intermediates 58 can be reacted with compounds of type 59, either commercially available or synthesized by methods known in the art and as described below to yield intermediates 60 (step b).

Compounds 60 can be further converted into compounds 61 by a deoxyfluorination reaction using a suitable fluorinating agent such as DAST, Deoxo-Fluor (bis(2-methoxyethyl)aminosulfur trifluoride) or aminodifluorosulfinium tetrafluoroborates (XtalFluor-E®, XtalFluor-M® in the presence of, e.g. triethylamine trihydrofluoride and TEA or DBU) in a suitable solvent such as DCM or ACN (step c).

Removal of the protective group from intermediates 61 applying literature methods and as described for example under Scheme 8, step c, furnishes intermediates 1 h (step d).

In case compounds 59 are commercially not available, they can be prepared in analogy to literature methods. For example, deprotonation of optionally substituted aryl or heteroaryl rings 62 using an appropriate base such nBuLi, secBuLi, tertBuLi, LiHMDS, NaH, KH in a suitable solvent, such as THF, n-hexane or mixtures thereof, at temperatures ranging from −78° C. to room temperature, gives intermediates 59 in which, depending on the base used, MX=Li, Na or K (step e).

Compounds 59 in which MX=MgHal with Hal being Cl, Br or I (Grignard reagents) may be prepared by reaction of the corresponding optionally substituted aryl or heteroaryl halides 63 via direct insertion of magnesium (e.g. magnesium turnings optionally in the presence of catalytic amounts of iodine, powder in the presence of LiCl or Rieke magnesium, organic halides) or by halogen-magnesium exchange by treating 63 in which Hal is preferably bromine or iodine, with an alkylmagnesium halide such as iPrMgCI (optionally in the presence of LiCl) in suitable solvents such as diethyl ether or THF at temperatures ranging from 0° C. to the boiling point of the solvent (step f).

In one aspect, the present invention provides a process of manufacturing a compound of formula (IA) or (IB) described herein, comprising:

(d) reacting an amine of formula 2, wherein X, Y, and Z are as described herein,

2

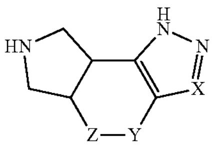

with a carboxylic acid 3a, wherein L, A, B, and $R^1$ to $R^3$ are as described herein 3a

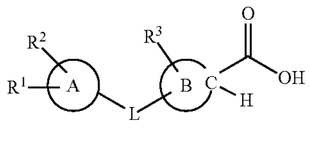

in the presence of a coupling reagent, such as CDI, DCC, HATU, HBTU, HOBT, TBTU, $T_3P$ or Mukaiyama reagent, and optionally in the presence of a base, such as TEA, DIPEA (Huenig's base) or DMAP, to form said compound of formula (IB), wherein X, Y, Z, L, A, B, and $R^1$ to $R^3$ are as defined herein (IB)

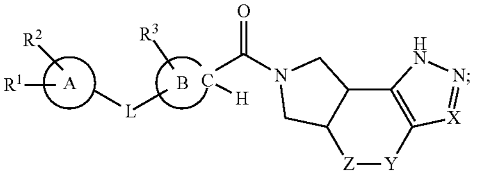

(e) reacting an amine of formula 2, wherein X, Y, and Z are as described herein,

2

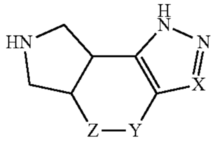

with a carboxylic acid chloride 3b, wherein L, A, B, and $R^1$ to $R^3$ are as described herein 3b

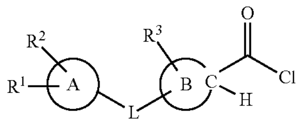

in the presence of a base, such as TEA, Huenig's base, pyridine, DMAP or lithium bis(trimethylsilyl)amide, to form said compound of formula (IB), wherein X, Y, Z, L, A, B, and $R^1$ to $R^3$ are as defined herein; or (f) reacting a first amine of formula 1, wherein A, B, L, and $R^1$ and $R^3$ are as described herein,

1

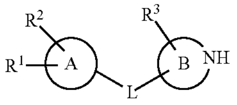

with a second amine 2, wherein X, Y, and Z are as described herein

2

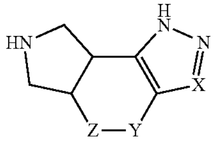

in the presence of a base, such as sodium bicarbonate, and a urea forming reagent, such as bis(trichloromethyl) carbonate, phosgene, trichloromethyl chloroformate, (4-nitrophenyl)carbonate or 1,1'-carbonyldiimidazole, to form said compound of formula (IA), wherein X, Y, Z, L, A, B, and $R^1$ to $R^3$ are as defined herein (IA)

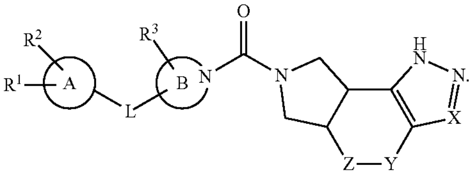

In one aspect, the present invention provides a compound of formula (I) as described herein, when manufactured according to any one of the processes described herein.

MAGL Inhibitory Activity

Compounds of the present invention are MAGL inhibitors. Thus, in one aspect, the present invention provides the use of compounds of formula (I) as described herein for inhibiting MAGL in a mammal.

In a further aspect, the present invention provides compounds of formula (I) as described herein for use in a method of inhibiting MAGL in a mammal.

In a further aspect, the present invention provides the use of compounds of formula (I) as described herein for the preparation of a medicament for inhibiting MAGL in a mammal.

In a further aspect, the present invention provides a method for inhibiting MAGL in a mammal, which method comprises administering an effective amount of a compound of formula (I) as described herein to the mammal.

Compounds were profiled for MAGL inhibitory activity by determining the enzymatic activity by following the hydrolysis of the natural substrate 2-arachidonoylglycerol resulting in arachidonic acid, which can be followed by mass spectrometry. This assay is hereinafter abbreviated "2-AG assay".

The 2-AG assay was carried out in 384 well assay plates (PP, Greiner Cat #784201) in a total volume of 20 μL. Compound dilutions were made in 100% DMSO (VWR Chemicals 23500.297) in a polypropylene plate in 3-fold dilution steps to give a final concentration range in the assay from 12.5 μM to 0.8 pM. 0.25 μL compound dilutions (100% DMSO) were added to 9 μL MAGL in assay buffer (50 mM TRIS (GIBCO, 15567-027), 1 mM EDTA (Fluka, 03690-100 mL), 0.01% (v/v) Tween. After shaking, the plate was incubated for 15 min at RT. To start the reaction, 10 μL 2-arachidonoylglycerol in assay buffer was added. The final concentrations in the assay was 50 pM MAGL and 8 μM 2-arachidonoylglyerol. After shaking and 30 min incubation at RT, the reaction was quenched by the addition of 40 μL of acetonitrile containing 4 μM of d8-arachidonic acid. The amount of arachidonic acid was traced by an online SPE system (Agilent Rapidfire) coupled to a triple quadrupole mass spectrometer (Agilent 6460). A C18 SPE cartridge (G9205A) was used in an acetonitrile/water liquid setup. The mass spectrometer was operated in negative electrospray mode following the mass transitions 303.1→259.1 for arachidonic acid and 311.1→267.0 for d8-arachidonic acid. The activity of the compounds was calculated based on the ratio of intensities [arachidonic acid/d8-arachidonic acid].

TABLE 1

| Example | $IC_{50}$ MAGL [nM] |
|---|---|
| 1 | 8 |
| 2 | 67 |
| 3 | 13 |

TABLE 1-continued

| Example | $IC_{50}$ MAGL [nM] |
|---|---|
| 4 | 917 |
| 5 | 488 |
| 6 | 9 |
| 7 | 50 |
| 8 | 523 |
| 9 | 2704 |
| 10 | 1217 |

In one aspect, the present invention provides compounds of formula (I) and their pharmaceutically acceptable salts or esters as described herein, wherein said compounds of formula (I) and their pharmaceutically acceptable salts or esters have $IC_{50}$'s for MAGL inhibition below 25 μM, preferably below 10 μM, more preferably below 5 μM as measured in the MAGL assay described herein.

In one embodiment, compounds of formula (I) and their pharmaceutically acceptable salts or esters as described herein have $IC_{50}$ (MAGL inhibition) values between 0.000001 μM and 25 μM, particular compounds have $IC_{50}$ values between 0.000005 μM and 10 μM, further particular compounds have $IC_{50}$ values between 0.00005 μM and 5 μM, as measured in the MAGL assay described herein.

Using the Compounds of the Invention

In one aspect, the present invention provides compounds of formula (I), or pharmaceutically acceptable salts thereof, as described herein for use as therapeutically active substance.

In a further aspect, the present invention provides the use of compounds of formula (I), or pharmaceutically acceptable salts thereof, as described herein for the treatment or prophylaxis of neuroinflammation, neurodegenerative diseases, pain, cancer, mental disorders and/or inflammatory bowel disease in a mammal.

In one embodiment, the present invention provides the use of compounds of formula (I), or pharmaceutically acceptable salts thereof, as described herein for the treatment or prophylaxis of neuroinflammation and/or neurodegenerative diseases in a mammal.

In one embodiment, the present invention provides the use of compounds of formula (I), or pharmaceutically acceptable salts thereof, as described herein for the treatment or prophylaxis of neurodegenerative diseases in a mammal.

In one embodiment, the present invention provides the use of compounds of formula (I), or pharmaceutically acceptable salts thereof, as described herein for the treatment or prophylaxis of cancer in a mammal.

In one embodiment, the present invention provides the use of compounds of formula (I), or pharmaceutically acceptable salts thereof, as described herein for the treatment or prophylaxis of inflammatory bowel disease in a mammal.

In one embodiment, the present invention provides the use of compounds of formula (I), or pharmaceutically acceptable salts thereof, as described herein for the treatment or prophylaxis of pain in a mammal.

In one aspect, the present invention provides the use of compounds of formula (I), or pharmaceutically acceptable salts thereof, as described herein for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain, spasticity associated with pain, abdominal pain, abdominal pain associated with irritable bowel syndrome and/or visceral pain in a mammal.

In a preferred embodiment, the present invention provides the use of compounds of formula (I), or pharmaceutically acceptable salts thereof, as described herein for the treatment or prophylaxis of multiple sclerosis, Alzheimer's disease and/or Parkinson's disease in a mammal.

In a particularly preferred embodiment, the present invention provides the use of compounds of formula (I), or pharmaceutically acceptable salts thereof, as described herein for the treatment or prophylaxis of multiple sclerosis in a mammal.

In one aspect, the present invention provides compounds of formula (I), or pharmaceutically acceptable salts thereof, as described herein for use in the treatment or prophylaxis of neuroinflammation, neurodegenerative diseases, pain, cancer, mental disorders and/or inflammatory bowel disease in a mammal.

In one embodiment, the present invention provides compounds of formula (I), or pharmaceutically acceptable salts thereof, as described herein for use in the treatment or prophylaxis of neuroinflammation and/or neurodegenerative diseases in a mammal.

In one embodiment, the present invention provides compounds of formula (I), or pharmaceutically acceptable salts thereof, as described herein for use in the treatment or prophylaxis of cancer in a mammal.

In one embodiment, the present invention provides compounds of formula (I), or pharmaceutically acceptable salts thereof, as described herein for use in the treatment or prophylaxis of neurodegenerative diseases in a mammal.

In one embodiment, the present invention provides compounds of formula (I), or pharmaceutically acceptable salts thereof, as described herein for use in the treatment or prophylaxis of inflammatory bowel disease in a mammal.

In one embodiment, the present invention provides compounds of formula (I), or pharmaceutically acceptable salts thereof, as described herein for use in the treatment or prophylaxis of pain in a mammal.

In one aspect, the present invention provides compounds of formula (I), or pharmaceutically acceptable salts thereof, as described herein for use in the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain, spasticity associated with pain, abdominal pain, abdominal pain associated with irritable bowel syndrome and/or visceral pain in a mammal.

In a preferred embodiment, the present invention provides compounds of formula (I), or pharmaceutically acceptable salts thereof, as described herein for use in the treatment or prophylaxis of multiple sclerosis, Alzheimer's disease and/or Parkinson's disease in a mammal.

In a particularly preferred embodiment, the present invention provides compounds of formula (I), or pharmaceutically acceptable salts thereof, as described herein for use in the treatment or prophylaxis of multiple sclerosis in a mammal.

In one aspect, the present invention provides the use of compounds of formula (I), or pharmaceutically acceptable salts thereof, as described herein for the preparation of a medicament for the treatment or prophylaxis of neuroinflammation, neurodegenerative diseases, pain, cancer, mental disorders and/or inflammatory bowel disease in a mammal.

In one embodiment, the present invention provides the use of compounds of formula (I), or pharmaceutically acceptable salts thereof, as described herein for the preparation of a medicament for the treatment or prophylaxis of neuroinflammation and/or neurodegenerative diseases in a mammal.

In one embodiment, the present invention provides the use of compounds of formula (I), or pharmaceutically acceptable salts thereof, as described herein for the preparation of a medicament for the treatment or prophylaxis of neurodegenerative diseases in a mammal.

In one embodiment, the present invention provides the use of compounds of formula (I), or pharmaceutically acceptable salts thereof, as described herein for the preparation of a medicament for the treatment or prophylaxis of cancer in a mammal.

In one embodiment, the present invention provides the use of compounds of formula (I), or pharmaceutically acceptable salts thereof, as described herein for the preparation of a medicament for the treatment or prophylaxis of inflammatory bowel disease in a mammal.

In one embodiment, the present invention provides the use of compounds of formula (I), or pharmaceutically acceptable salts thereof, as described herein for the preparation of a medicament for the treatment or prophylaxis of pain in a mammal.

In a further aspect, the present invention provides the use of compounds of formula (I), or pharmaceutically acceptable salts thereof, as described herein for the preparation of a medicament for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain, spasticity associated with pain, abdominal pain, abdominal pain associated with irritable bowel syndrome and/or visceral pain in a mammal.

In a preferred embodiment, the present invention provides the use of compounds of formula (I), or pharmaceutically acceptable salts thereof, as described herein for the preparation of a medicament for the treatment or prophylaxis of multiple sclerosis, Alzheimer's disease and/or Parkinson's disease in a mammal.

In a particularly preferred embodiment, the present invention provides the use of compounds of formula (I), or pharmaceutically acceptable salts thereof, as described herein for the preparation of a medicament for the treatment or prophylaxis of multiple sclerosis in a mammal.

In one aspect, the present invention provides a method for the treatment or prophylaxis of neuroinflammation, neurodegenerative diseases, pain, cancer, mental disorders and/or inflammatory bowel disease in a mammal, which method comprises administering an effective amount of a compound of formula (I), or a pharmaceutically acceptable salt thereof, as described herein to the mammal.

In one embodiment, the present invention provides a method for the treatment or prophylaxis of neuroinflammation and/or neurodegenerative diseases in a mammal, which method comprises administering an effective amount of a compound of formula (I), or a pharmaceutically acceptable salt thereof, as described herein to the mammal.

In one embodiment, the present invention provides a method for the treatment or prophylaxis of neurodegenerative diseases in a mammal, which method comprises administering an effective amount of a compound of formula (I), or a pharmaceutically acceptable salt thereof, as described herein to the mammal.

In one embodiment, the present invention provides a method for the treatment or prophylaxis of cancer in a mammal, which method comprises administering an effective amount of a compound of formula (I), or a pharmaceutically acceptable salt thereof, as described herein to the mammal.

In one embodiment, the present invention provides a method for the treatment or prophylaxis of inflammatory bowel disease in a mammal, which method comprises administering an effective amount of a compound of formula (I), or a pharmaceutically acceptable salt thereof, as described herein to the mammal.

In one embodiment, the present invention provides a method for the treatment or prophylaxis of pain in a mammal, which method comprises administering an effective amount of a compound of formula (I), or a pharmaceutically acceptable salt thereof, as described herein to the mammal.

In a further aspect, the present invention provides a method for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain, spasticity associated with pain, abdominal pain, abdominal pain associated with irritable bowel syndrome and/or visceral pain in a mammal, which method comprises administering an effective amount of a compound of formula (I), or a pharmaceutically acceptable salt thereof, as described herein to the mammal.

In a preferred embodiment, the present invention provides a method for the treatment or prophylaxis of multiple sclerosis, Alzheimer's disease and/or Parkinson's disease in a mammal, which method comprises administering an effective amount of a compound of formula (I), or a pharmaceutically acceptable salt thereof, as described herein to the mammal.

In a particularly preferred embodiment, the present invention provides a method for the treatment or prophylaxis of multiple sclerosis in a mammal, which method comprises administering an effective amount of a compound of formula (I), or a pharmaceutically acceptable salt thereof, as described herein to the mammal.

Pharmaceutical Compositions and Administration

In one aspect, the present invention provides a pharmaceutical composition comprising a compound of formula (I) as described herein and a therapeutically inert carrier.

In one embodiment, the present invention provides the pharmaceutical compositions disclosed in Examples 11 and 12.

The compounds of formula (I) and their pharmaceutically acceptable salts and esters can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts and esters can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules are, for example, vegetable oils, waxes, fats, semi solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

EXAMPLES

The invention will be more fully understood by reference to the following examples. The claims should not, however, be construed as limited to the scope of the examples.

In case the preparative examples are obtained as a mixture of enantiomers, the pure enantiomers can be separated by methods described herein or by methods known to the man skilled in the art, such as e.g., chiral chromatography (e.g. chiral SFC) or crystallization.

All reaction examples and intermediates were prepared under an argon atmosphere if not specified otherwise.

The invention will be more fully understood by reference to the following examples. The claims should not, however, be construed as limited to the scope of the examples.

In case the preparative examples are obtained as a mixture of enantiomers, the pure enantiomers can be separated by methods described herein or by methods known to the man skilled in the art, such as e.g., chiral chromatography (e.g. chiral SFC) or crystallization.

All reaction examples and intermediates were prepared under an argon atmosphere if not specified otherwise.

Example 1

[3-[[2-Fluoro-4-(trifluoromethyl)phenyl]methoxy]azetidin-1-yl]-[rac-(5aR,8aS)-4,5,5a,6,8,8a-hexahydro-1H-pyrrolo[3,4-g]indazol-7-yl]methanone

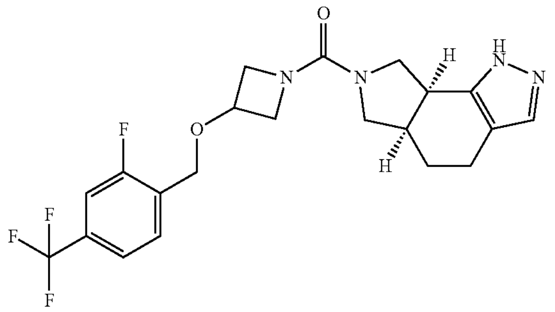 [SMILES: O=C(N1CC(OCc2ccc(C(F)(F)F)cc2F)C1)N1C[C@@H]2CCc3cn[nH]c3[C@@H]2C1]

To a suspension of 3-[[2-fluoro-4-(trifluoromethyl)phenyl]methoxy]azetidine 4-methylbenzenesulfonic acid (120 mg, 285 μmol, 1.0 equiv; CAS RN 2135785-94-1) in ACN (1 mL) was added TEA (202 mg, 279 μL, 2 mmol, 7.0 equiv) followed by addition of di(1H-1,2,4-triazol-1-yl)methanone (46.9 mg, 285 μmol, 1.0 equiv; CAS RN 41864-22-6) in one portion. The mixture was stirred at RT for 60 min. After addition of a solution of rac-(5aR,8aS)-1,4,5,5a,6,7,8,8a-octahydropyrrolo[3,4-g]indazole hydrochloride (114 mg, 285 μmol, 1.0 equiv; BB 1) in ACN (0.5 mL), the mixture was stirred at 70° C. for 20 h. The reaction mixture was completely evaporated and the product was purified by preparative HPLC (Gemini NX column) using a gradient of ACN:water (containing 0.1% TEA) (20:80 to 98:2) to yield the title compound as a colorless foam (12 mg, 10%). MS (ESI): m/z=439.3 $[M+H]^+$.

Example 2

[3-[[2-Fluoro-4-(trifluoromethyl)phenyl]methoxy]azetidin-1-yl]-[rac-(1S,9R)-7-oxa-3,4,11-triazatricyclo[7.3.0.0$^{2,6}$]dodeca-2(6),4-dien-11-yl]methanone

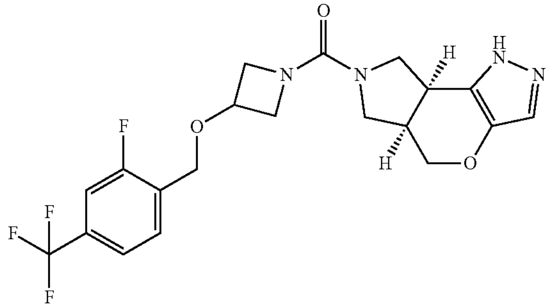 [SMILES: O=C(N1CC(OCc2ccc(C(F)(F)F)cc2F)C1)N1C[C@@H]2COc3cn[nH]c3[C@@H]2C1]

To a turbid solution of rac-(1S,9R)-7-oxa-3,4,11-triazatricyclo[7.3.0.0$^{26}$]dodeca-2(6),4-diene (44 mg, 266 μmol, 1.0 equiv; BB 2) in ACN (1 mL) was added TEA (260 μL, 1.86 mmol, 7.0 equiv) followed by addition of di(1H-1,2,4-triazol-1-yl)methanone (43.7 mg, 266 μmol, 1.0 equiv) in one portion. The suspension was stirred at RT for 1.25 h. After addition of 3-[[2-fluoro-4-(trifluoromethyl)phenyl]methoxy]azetidine 4-methylbenzenesulfonic acid (112 mg, 266 μmol, 1.0 equiv; CAS RN 2135785-94-1) stirring was continued at 50° C. overnight. The reaction mixture was evaporated, the residue taken up in water and EtOAc and the layers were separated. The aqueous layer was extracted twice with EtOAc. The organic layers were washed once with water, dried over $MgSO_4$, filtered, treated with silica gel and evaporated. The compound was purified by silica gel chromatography on a 4 g column using an MPLC system eluting with a gradient of n-heptane:EtOAc/EtOH 3/1 (100:0 to 0:100). Another purification by silica gel chromatography on a 4 g column using an MPLC (ISCO) system eluting with a gradient of DCM:MeOH (100:0 to 90:10) yielded the title compound as a colorless solid (24 mg, 21%). MS (ESI): m/z=441.3 $[M+H]^+$.

Example 3 and Example 4

(−)- or (+)-[(1S,9R)-7-Oxa-3,4,11-triazatricyclo[7.3.0.0$^{2,6}$]dodeca-2(6),4-dien-11-yl]-[3-[4-[1-(trifluoromethyl)cyclopropyl]phenyl]azetidin-1-yl]methanone

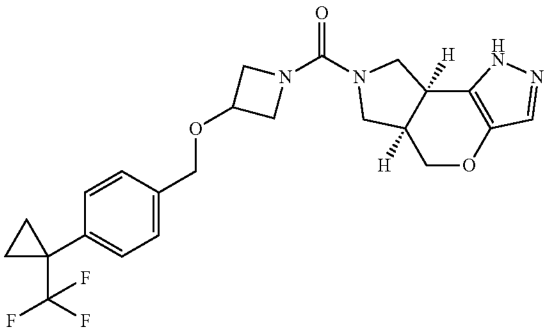 [SMILES: O=C(N1CC(OCc2ccc(C3(C(F)(F)F)CC3)cc2)C1)N1C[C@@H]2COc3cn[nH]c3[C@@H]2C1]

and (+)- or (−)-[(1R,9S)-7-Oxa-3,4,11-triazatricyclo[7.3.0.0$^{2,6}$]dodeca-2(6),4-dien-11-yl]-[3-[4-[1-(trifluoromethyl)cyclopropyl]phenyl]azetidin-1-yl]methanone

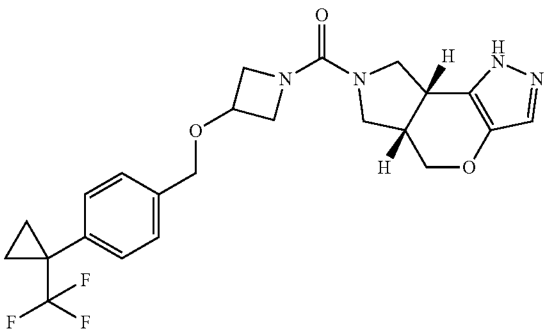 [SMILES: O=C(N1CC(OCc2ccc(C3(C(F)(F)F)CC3)cc2)C1)N1C[C@H]2COc3cn[nH]c3[C@H]2C1]

To a turbid solution of rac-(1S,9R)-7-oxa-3,4,11-triazatricyclo[7.3.0.0$^{2,6}$]dodeca-2(6),4-diene (100 mg, 605 μmol, 1.0 equiv; BB 2) in ACN (2.5 mL) was added TEA (591 μL, 4.24 mmol, 7.0 equiv) followed by addition of di(1H-1,2,4-triazol-1-yl)methanone (99.4 mg, 605 μmol, 1.0 equiv) in one portion. The suspension was stirred at RT for 1.25 h to give a clear solution. After addition of 3-(4-(1-(trifluoromethyl)cyclopropyl)phenyl)azetidine 4-methylbenzenesulfonate (250 mg, 605 μmol, 1.0 equiv; BB 3) stirring was continued at 50° C. overnight. The reaction mixture was evaporated. The residue was taken up in water and EtOAc and the layers were separated. The aqueous layer was extracted twice with EtOAc. The organic layers were washed once with water, dried over $MgSO_4$, filtered and evaporated. The racemic product was separated on a preparative SFC (OJ-H column) using an isocratic mixture of MeOH:carbon dioxide (15:85) to give (−)- or (+)-[(1S,9R)-7-oxa-3,4,11-triazatricyclo[7.3.0.02,6]dodeca-2(6),4-dien-11-yl]-[3-[4-[1-(trifluoromethyl)cyclopropyl]phenyl]azetidin-1-yl]methanone (57 mg, 22%; first eluting compound) as a colorless solid (MS (ESI): m/z=433.3 $[M+H]^+$) and (+)- or (−)-[(1R,9S)-7-oxa-3,4,11-triazatricyclo[7.3.0.02,6]dodeca-2(6),4-dien-11-yl]-[3-[4-[1-(trifluoromethyl)cyclopropyl]phenyl]azetidin-1-yl]methanone (59 mg, 23%; second eluting compound) as a colorless solid (MS (ESI): m/z=433.3 $[M+H]^+$).

Example 5 and Example 6

(−)- or (+)-[6-[(2,4-Difluorophenyl)methyl]-2-azaspiro[3.3]heptan-2-yl]-[(1S,9R)-7-oxa-3,4,11-triazatricyclo[7.3.0.0$^{2,6}$]dodeca-2(6),4-dien-11-yl]methanone

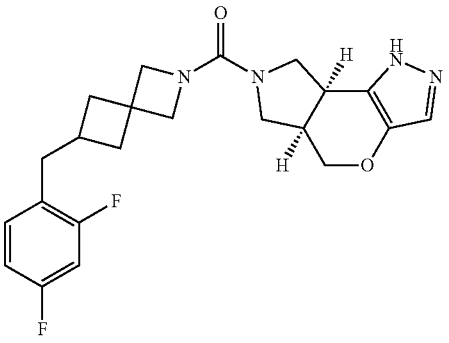 [SMILES: O=C(N1C[C@@H]2COc3cn[nH]c3[C@@H]2C1)N1CC2(CC(Cc3ccc(F)cc3F)C2)C1]

and (+)- or (−)-[6-[(2,4-Difluorophenyl)methyl]-2-azaspiro[3.3]heptan-2-yl]-[(1R,9S)-7-oxa-3,4,11-triazatricyclo[7.3.0.0$^{2,6}$]dodeca-2(6),4-dien-11-yl]methanone

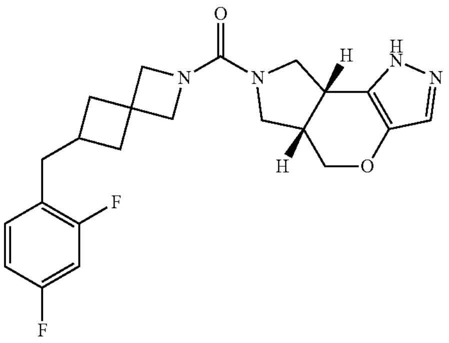 [SMILES: O=C(N1C[C@H]2COc3cn[nH]c3[C@H]2C1)N1CC2(CC(Cc3ccc(F)cc3F)C2)C1]

To a turbid solution of rac-(1S,9R)-7-oxa-3,4,11-triazatricyclo[7.3.0.0$^{2,6}$]dodeca-2(6),4-diene (64 mg, 387 μmol, 1.0 equiv; BB 2) in ACN (1.5 mL) was added TEA (392 mg, 540 μL, 3.87 mmol, 10.0 equiv) followed by addition of di(1H-1,2,4-triazol-1-yl)methanone (63.6 mg, 387 μmol, 1.0 equiv) in one portion. The suspension was stirred at RT for 1.25 h to give a clear solution. After addition of a solution of 6-[(2,4-difluorophenyl)methyl]-2-azaspiro[3.3]heptane 2,2,2-trifluoroacetic acid (131 mg, 387 μmol, 1.0 equiv; BB 4) in DCM (1.5 mL), stirring was continued at 50° C. overnight. The reaction mixture was evaporated. The residue was taken up in water and EtOAc and the layers were separated. The aqueous layer was extracted twice with EtOAc. The organic layers were washed once with water, dried over $MgSO_4$, filtered and evaporated. The product was purified by preparative HPLC (Gemini NX column) using a gradient of ACN:water (containing 0.1% TEA) (20:80 to 98:2). The racemic product (colorless oil, 40 mg) was separated by preparative chiral HPLC (Chiralpak-NR column) using an isocratic mixture of EtOH (containing 0.8% $NH_4OAc$):n-heptane (60:40) to give (−)- or (+)-[6-[(2,4-difluorophenyl)methyl]-2-azaspiro[3.3]heptan-2-yl]-[(1 S,9R)-7-oxa-3,4,11-triazatricyclo[7.3.0.02,6]dodeca-2(6),4-dien-11-yl]methanone (13 mg, 8%; first eluting compound) as a colorless solid (MS (ESI): m/z=415.3 $[M+H]^+$) and (+)- or (−)-[6-[(2,4-difluorophenyl)methyl]-2-azaspiro[3.3]heptan-2-yl]-[(1R,9S)-7-oxa-3,4,11-triazatricyclo[7.3.0.02,6]dodeca-2(6),4-dien-11-yl]methanone (13 mg, 8%; second eluting compound) as a colorless solid (MS (ESI): m/z=415.3 $[M+H]^+$).

Example 7 and Example 8

(−)- or (+)-[3-[[2-Fluoro-4-(trifluoromethyl)phenyl]methoxy]azetidin-1-yl]-[(5aR,8aS)-4,5,5a,6,8,8a-hexahydro-1H-pyrrolo[3,4-e]benzotriazol-7-yl]methanone

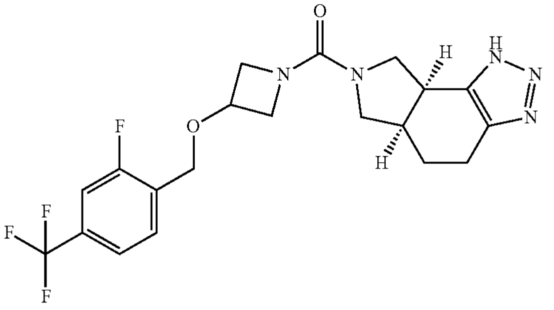 [SMILES: O=C(N1CC(OCc2ccc(C(F)(F)F)cc2F)C1)N1C[C@@H]2CCc3nn[nH]c3[C@@H]2C1]

and (+)- or (−)-[3-[[2-Fluoro-4-(trifluoromethyl)phenyl]methoxy]azetidin-1-yl]-[(5aS,8aR)-4,5,5a,6,8,8a-hexahydro-1H-pyrrolo[3,4-e]benzotriazol-7-yl]methanone

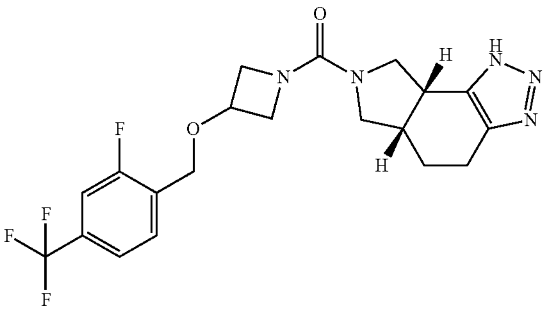 [SMILES: O=C(N1CC(OCc2ccc(C(F)(F)F)cc2F)C1)N1C[C@H]2CCc3nn[nH]c3[C@H]2C1]

To a turbid solution of rac-(5aR,8aS)-1,4,5,5a,6,7,8,8a-octahydropyrrolo[3,4-e]benzotriazole (90 mg, 548 μmol, 1.0 equiv; BB 5) in MeCN (2 mL) was added TEA (535 μL, 3.84 mmol, 7.0 equiv) followed by addition of di(1H-1,2,4-triazol-1-yl)methanone (90 mg, 548 μmol, 1.0 equiv) in one portion. The suspension was stirred at RT for 1.25 h to give a clear solution. After addition of 3-[[2-fluoro-4-(trifluoromethyl)phenyl]methoxy]azetidine 4-methylbenzenesulfonic acid (231 mg, 548 μmol, 1.0 equiv; CAS RN 2135785-94-1) stirring was continued at 50° C. overnight. The reaction mixture was evaporated. The residue was taken up in water and EtOAc and the layers were separated. The aqueous layer was extracted twice with EtOAc. The organic layers were washed once with water, dried over $MgSO_4$, filtered and evaporated. The racemic product was separated by preparative SFC (AD-H column) using an isocratic mixture of MeOH:carbon dioxide (30:70) to give (−)- or (+)-[3-[[2-fluoro-4-(trifluoromethyl)phenyl]methoxy]azetidin-1-yl]-[(5 aR, 8aS)-4,5,5a,6,8,8a-hexahydro-1H-pyrrolo[3,4-e]benzotriazol-7-yl]methanone (66 mg, 27%; first eluting compound) as a light brown solid (MS (ESI): m/z=440.4 $[M+H]^+$) and (+)- or (−)-[3-[[2-fluoro-4-(trifluoromethyl)phenyl]methoxy]azetidin-1-yl]-[(5aS,8aR)-4,5,5a,6,8,8a-hexahydro-1H-pyrrolo[3,4-e]benzotriazol-7-yl]methanone (55 mg, 22%; second eluting compound) as a light brown solid (MS (ESI): m/z=440.4 $[M+H]^+$).

Example 9 and Example 10

(−)- or (+)-[3-[[2-Fluoro-4-(trifluoromethyl)phenyl]methoxy]azetidin-1-yl]-[(1S,9R)-8-oxa-3,4,5,11-tetrazatricyclo[7.3.0.02,6]dodeca-2(6),4-dien-11-yl]methanone

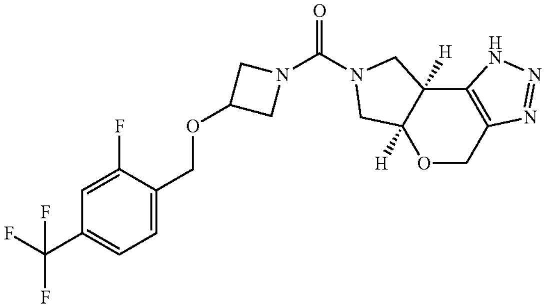 [SMILES: O=C(N1CC(OCc2ccc(C(F)(F)F)cc2F)C1)N1C[C@@H]2OCc3nn[nH]c3[C@@H]2C1]

and (+)- or (−)-[3-[[2-Fluoro-4-(trifluoromethyl)phenyl]methoxy]azetidin-1-yl]-[(1R,9S)-8-oxa-3,4,5,11-tetrazatricyclo[7.3.0.02,6]dodeca-2(6),4-dien-11-yl]methanone

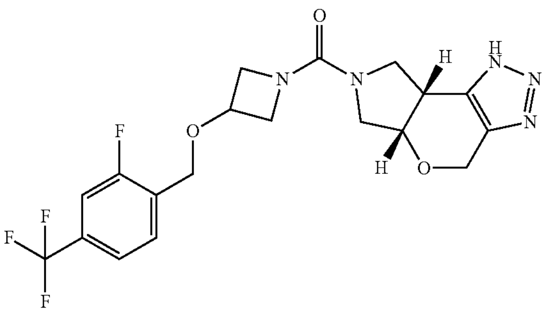 [SMILES: O=C(N1CC(OCc2ccc(C(F)(F)F)cc2F)C1)N1C[C@@H]2c3[nH]nnc3CO[C@@H]2C1]

To a turbid solution of rac-(1S,9R)-8-oxa-3,4,5,11-tetrazatricyclo[7.3.0.$0^{2,6}$]dodeca-2(6),4-diene (73 mg, 439 μmol, 1.0 equiv; BB 6) in MeCN (1.5 mL) was added TEA (429 μL, 3.08 mmol, 7.0 equiv) followed by addition of di(1H-1,2,4-triazol-1-yl)methanone (72.1 mg, 439 μmol, 1.0 equiv) in one portion. The suspension was stirred at RT for 2 h. After addition of 3-[[2-fluoro-4-(trifluoromethyl)phenyl]methoxy]azetidine 4-methylbenzenesulfonic acid (185 mg, 439 μmol, 1.0 equiv; CAS RN 2135785-94-1) stirring was continued at 50° C. for 1.5 h. A suspension formed, which after cooling to RT was filtered. The product was purified by preparative HPLC (Gemini NX column) using a gradient of ACN:water (containing 0.1% TEA) (20:80 to 98:2). The racemic product was separated by preparative SFC (AD-H column) using an isocratic mixture of MeOH: carbon dioxide (30:70) to give (−)- or (+)-[3-[[2-fluoro-4-(trifluoromethyl)phenyl]methoxy]azetidin-1-yl]-[(1 S,9R)-8-oxa-3,4,5,11-tetrazatricyclo[7.3.0.02,6]dodeca-2(6),4-dien-11-yl]methanone (53 mg, 27%; first eluting compound) as a light brown solid (MS (ESI): m/z=442.3 $[M+H]^+$) and (+)- or (−)-[3-[[2-fluoro-4-(trifluoromethyl)phenyl]methoxy]azetidin-1-yl]-[(1R,9S)-8-oxa-3,4,5,11-tetrazatricyclo[7.3.0.02,6]dodeca-2(6),4-dien-11-yl]methanone (29 mg, 15%; second eluting compound) as a light brown solid (MS (ESI): m/z=442.3 $[M+H]^+$).

Synthesis of Building Blocks

BB 1 rac-(5aR,8aS)-1,4,5,5a,6,7,8,8a-Octahydropyrrolo[3,4-g]indazole hydrochloride

Step 1: rac-(3aS,5Z,7aR)-2-Benzyl-5-(dimethylaminomethylene)-1,3,3a,6,7,7a-hexahydroisoindol-4-one To a solution of rac-(3aR,7aS)-2-benzyloctahydro-4H-isoindol-4-one (200 mg, 872 μmol, 1.0 equiv; CAS RN 163484-15-9) in anhydrous toluene (1.5 mL) under Ar was added 1,1-dimethoxy-N,N-dimethylmethanamine (232 μL, 1.74 mmol, 2.0 equiv; CAS RN 4637-24-5) and the mixture was stirred at 111° C. for 3 h in a sealed tube and at 130° C. for 19 h. After cooling to RT the solution was evaporated and the light brown oil was used in the next step without further purification.

Step 2: rac-(5aR,8aS)-7-Benzyl-4,5,5a,6,8,8a-hexahydro-1H-pyrrolo[3,4-g]indazole To a solution of rac-(3aS,5Z,7aR)-2-benzyl-5-(dimethylaminomethylene)-1,3,3a,6,7,7a-hexahydroisoindol-4-one (248 mg, 872 μmol, 1.0 equiv) and hydrazine dihydrochloride (91.5 mg, 872 μmol, 1.0 equiv) in MeOH was added dropwise at 0° C. NaOH (1.74 ml, 3.49 mmol, 4.0 equiv; 2 M in water) and the mixture was stirred at 77° C. in a sealed tube. The reaction mixture was poured on half-saturated aqueous $NH_4Cl$ solution and EtOAc and the layers were separated. The aqueous layer was extracted twice with EtOAc. The organic layers were washed once with brine, dried over $MgSO_4$, filtered and evaporated to provide the desired compound as a yellow foam (147 mg, 57%). MS (ESI): m/z=254.2 $[M+H]^+$.BB 2 rac-(1S,9R)-7-Oxa-3,4,11-triazatricyclo[7.3.0.$0^{2,6}$]dodeca-2(6),4-diene

Step 1: rac-(3aR,7aS)-2-Benzyl-3,3a,4,7a-tetrahydro-1H-pyrano[3,4-c]pyrrol-7-one To a solution of N-benzyl-1-methoxy-N-((trimethylsilyl)methyl)methanamine (2 mL, 7.82 mmol, 1.05 equiv; CAS RN 93102-05-7) and 2H-pyran-3(6H)-one (729 mg, 7.43 mmol, 1.0 equiv; CAS RN 98166-23-5) in anhydrous toluene (20 mL) was added TFA (57.2 μL, 743 μmol, 1.0 equiv) and the mixture was stirred at RT for 18 h. To the clear, light yellow solution was added TEA (104 μL, 743 μmol, 0.1 equiv) and the mixture was treated with silica gel and evaporated. The compound was purified by silica gel chromatography on a 40 g column using an MPLC system eluting with a gradient of n-heptane:EtOAc/EtOH 3/1 (100:0 to 0:100) to get the desired compound as a yellow oil (1.15 g, 61%). MS (ESI): m/z=232.2 $[M+H]^+$.

Step 2: rac-(3aR,6E,7aS)-2-Benzyl-6-(dimethylaminomethylene)-3,3a,4,7a-tetrahydro-1H-pyrano[3,4-c]pyrrol-7-one To a solution of rac-(3aR,7aS)-2-benzyl-3,3a,4,7a-tetrahydro-1H-pyrano[3,4-c]pyrrol-7-one (395 mg, 1.71 mmol, 1.0 equiv) in anhydrous toluene (3 mL) under argon was added 1,1-dimethoxy-N,N-dimethylmethanamine (454 μL, 3.42 mmol, 2.0 equiv; CAS RN 4637-24-5) and the mixture was stirred at 130° C. overnight. The solution was evaporated to provide the desired compound as a brown oil (515 mg) which was used in the next step without further purification. MS (ESI): m/z=287.3 $[M+H]^+$.

Step 3: rac-(1S,9R)-11-Benzyl-7-oxa-3,4,11-triazatricyclo[7.3.0.$0^{2,6}$]dodeca-2(6),4-diene A mixture of rac-(3aR,6E,7aS)-2-benzyl-6-(dimethylaminomethylene)-3,3a,4,7a-tetrahydro-1H-pyrano[3,4-c]pyrrol-7-one (480 mg, 1.68 mmol, 1.0 equiv) and hydrazine monohydrate (122 μL, 2.51 mmol, 1.5 equiv) in EtOH (1 mL) was heated at 85° C. in a sealed tube for 2 h. Silica gel was added and the suspension was evaporated. The compound was purified by silica gel chromatography on a 12 g column using an MPLC (ISCO) system eluting with a gradient of n-heptane:EtOAc/EtOH 3/1 (80:20 to 0:100) to furnish the desired compound as a light yellow gum (89 mg, 21%). MS (ESI): m/z=256.3 $[M+H]^+$.

Step 4: rac-(1S,9R)-7-Oxa-3,4,11-triazatricyclo[7.3.0.02,6]dodeca-2(6),4-diene To a solution of rac-(1S,9R)-11-Benzyl-7-oxa-3,4,11-triazatricyclo[7.3.0.$0^{2,6}$]dodeca-2(6),4-diene (85 mg, 333 μmol, 1.0 equiv) in MeOH (2 mL) and EtOAc (1 mL) was added Pd/C (20 mg, 18.8 μmol, 0.06 equiv; wt. 10%) and the mixture was stirred under a hydrogen atmosphere at 50° C. and 20 bar for 19 h. The suspension was allowed to cool down to RT and filtered. The filtrate was completely evaporated to yield a colorless oil (55 mg, 100%) which was used in the next step without further purification. MS (ESI): m/z=166.1 $[M+H]^+$.

BB 3

3-(4-(1-(Trifluoromethyl)cyclopropyl)phenyl)azetidine 4-methylbenzenesulfonate

A mixture of tert-butyl 3-(4-(1-(trifluoromethyl)cyclopropyl)phenyl)azetidine-1-carboxylate (12.23 g, 35.8 mmol, 1.0 equiv; CAS RN 2377009-83-9) and p-toluenesulfonic acid monohydrate (7.16 g, 37.6 mmol, 1.05 equiv) in EtOAc (122 mL) was heated at reflux for 1 h. The suspension was cooled in an ice-bath over 2 h and then filtered. The filter cake was washed with a small volume of cold EtOAc (20 mL) to provide the desired compound as a colorless solid (13.4 g, 90%). MS (ESI): m/z=242.2 $[M+H]^+$.

BB 4

6-[(2,4-Difluorophenyl)methyl]-2-azaspiro[3.3]heptane 2,2,2-trifluoroacetic acid Step 1: (2,4-Difluorophenyl)methyl-triphenylphosphonium bromide A mixture of triphenylphosphine (1.27 g, 4.83 mmol, 1.0 equiv) and 1-(bromomethyl)-2,4-difluorobenzene (1.0 g, 620 µl, 4.83 mmol, 1.0 equiv) in MeCN (10 mL) was stirred at 80° C. for 3 h. The mixture was allowed to cool down to RT and TBME (100 mL) was added. The solid was filtered off and washed with some TBME to provide the desired compound as a colorless solid (2.18 g, 96%). MS (ESI): m/z=389.2 $[M-Br]^+$.

Step 2: tert-Butyl 6-[(4,6-difluorocyclohexa-2,4-dien-1-yl)methylene]-2-azaspiro[3.3]heptane-2-carboxylate To a solution of (2,4-difluorophenyl)methyl-triphenylphosphonium bromide (1.7 g, 3.62 mmol, 1.0 equiv) in dry THF (10 mL) at −78° C. was added LHMDS (7.24 ml, 7.24 mmol, 2.0 equiv; 1 M in THF). The reaction mixture was stirred at −78° C. for 2 h. The mixture was allowed to warm to ice-bath temperature. Between 2-5° C., tert-butyl 6-oxo-2-azaspiro[3.3]heptane-2-carboxylate (1.53 g, 7.24 mmol, 2.0 equiv; CAS RN 1181816-12-5) was added and the mixture was stirred at 85° C. overnight. After cooling down to RT, TBME was added and the formed suspension was filtered. The filtrate was evaporated and the residue purified by silica gel chromatography on a 50 g column using an MPLC system eluting with a gradient of n-heptane: EtOAc (100:0 to 30:70) to yield the desired compound as a colorless solid (352 mg, 30%). MS (ESI): m/z=266.2 $[M+2H-tBu]^+$.

Step 3: tert-Butyl 6-[(2,4-difluorophenyl)methyl]-2-azaspiro[3.3]heptane-2-carboxylate To a solution of tert-butyl 6-[(4,6-difluorocyclohexa-2,4-dien-1-yl)methylene]-2-azaspiro[3.3]heptane-2-carboxylate (350 mg, 1.09 mmol, 1.0 equiv) in EtOAc (10 mL) was added Pd/C (116 mg, 109 µmol, 0.1 equiv; wt. 10%) and the mixture was stirred under an atmosphere of hydrogen (1 bar) at RT for 2 h. The suspension was filtered and the filtrate was evaporated to furnish the desired compound as a colorless solid (345 mg, 98%). MS (ESI): m/z=268.2 $[M+2H-tBu]^+$.

Step 4: 6-[(2,4-Difluorophenyl)methyl]-2-azaspiro[3.3]heptane 2,2,2-trifluoroacetic acid To a solution of tert-butyl 6-[(2,4-difluorophenyl)methyl]-2-azaspiro[3.3]heptane-2-carboxylate (55 mg, 170 µmol, 1.0 equiv) in DCM (1 mL) was added TFA (52.4 µL, 680 µmol, 4.0 equiv) and the solution was stirred at RT for 20 h. The mixture was evaporated to dryness. The residue was mixed with anhydrous toluene and evaporated to provide the desired product that was used in the next step without further purification. MS (ESI): m/z=224.2 $[M+H]^+$.

BB 5 rac-(5aR,8aS)-1,4,5,5a,6,7,8,8a-Octahydropyrrolo[3,4-e]benzotriazole

Step 1: rac-(5aR,8aS)-7-(Cyclohexa-2,4-dien-1-ylmethyl)-4,5,5a,6,8,8a-hexahydro-1H-pyrrolo[3,4-e]benzotriazole To a mixture of rac-(3aR,7aS)-2-benzyloctahydro-4H-isoindol-4-one (215 mg, 938 µmol, 1.0 equiv; CAS RN 163484-15-9) and 1-azido-4-nitrobenzene (200 mg, 1.22 mmol, 1.3 equiv; CAS RN 1516-60-5) in DMF (2 mL) under Ar was added ammonium acetate (361 mg, 4.69 mmol, 5.0 equiv) and the dark solution was stirred at 80° C. for 4 h. The reaction mixture was poured on water and EtOAc and the layers were separated. The aqueous layer was extracted twice with EtOAc. No clear distribution of the desired product into the organic phase. Therefore all layers were evaporated and combined. The product was purified by preparative HPLC (Gemini NX column) using a gradient of ACN:water (containing 0.1% TEA) (20:80 to 98:2) to yield the desired compound as a light brown gum (39 mg; 16%). MS (ESI): m/z=255.3 $[M+4]^+$.

Step 2: rac-(5aR,8aS)-1,4,5,5a,6,7,8,8a-Octahydropyrrolo[3,4-e]benzotriazole

To a solution of rac-(5aR,8aS)-7-(cyclohexa-2,4-dien-1-ylmethyl)-4,5,5a,6,8,8a-hexahydro-1H-pyrrolo[3,4-e]benzotriazole (153 mg, 602 µmol, 1.0 equiv) in MeOH (3 mL) was added Pd/C (18 mg, 16.9 µmol, 0.03 equiv; wt. 10%) and the mixture was stirred under an atmosphere of hydrogen (20 bar) at 60° C. for 18 h. The suspension was allowed to cool down to RT and filtered. The filtrate solution was completely evaporated to yield a colorless oil (93 mg, 94%) that was used in the next step without further purification. MS (ESI): m/z=165.1 $[M+H]^+$.

BB 6 rac-(1S,9R)-8-Oxa-3,4,5,11-tetrazatricyclo[$7.3.0.0^{2,6}$]dodeca-2(6),4-diene

Step 1: rac-(4aR,7aR)-6-Benzyl-4a,5,7,7a-tetrahydropyrano[2,3-c]pyrrol-4-one

A solution of 4H-pyran-4-one (2.75 g, 28.6 mmol, 1.0 equiv; CAS RN 108-97-4) and N-benzyl-1-methoxy-N-((trimethylsilyl)methyl)methanamine (7.32 mL, 28.6 mmol, 1.0 equiv) in MeCN (12 mL) under Ar was stirred at 44° C. for 40 h. Another batch of N-benzyl-1-methoxy-N-((trimethylsilyl)methyl)methanamine (3.66 mL, 14.3 mmol, 0.5 equiv) was then added and stirring was continued at 44° C. over the weekend. After 88 h, silica gel was added and the mixture was evaporated. The compound was purified by silica gel chromatography on a 40 g column using an MPLC (ISCO) system eluting with a gradient of n-heptane:EtOAc (100:0 to 0:100). A second purification step using silica gel chromatography on a 40 g column using an MPLC (ISCO) system eluting with a gradient of n-heptane:EtOAc (100:0 to 20:80) furnished the desired compound as a light brown oil (0.92 g, 13%). MS (ESI): m/z=230.2 $[M+H]^+$.

Step 2: rac-(4aR,7aR)-6-Benzyl-2,3,4a,5,7,7a-hexahydropyrano[2,3-c]pyrrol-4-one

To a solution of rac-(4aR,7aR)-6-benzyl-4a,5,7,7a-tetrahydropyrano[2,3-c]pyrrol-4-one (1.2 g, 5.23 mmol, 1.0 equiv) in EtOAc (5 mL) and MeOH (5 mL) was added Pd/C (111 mg, 105 μmol, 0.02 equiv; wt. 10%). The suspension was stirred under a hydrogen atmosphere (1 bar) at RT overnight and then filtered. The filtrate was treated with silica gel and evaporated. The compound was purified by silica gel chromatography on a 12 g column using an MPLC system eluting with a gradient of n-heptane:EtOAc (100:0 to 0:100) to provide the desired compound as a light brown oil (0.41 g, 30%). MS (ESI): m/z=232.2 $[M+H]^+$.

Step 3: rac-(1S,9R)-11-Benzyl-8-oxa-3,4,5,11-tetrazatricyclo[7.3.0.0$^{2,6}$]dodeca-2(6),4-diene To a mixture of rac-(4aR,7aR)-6-benzyl-2,3,4a,5,7,7a-hexahydropyrano[2,3-c]pyrrol-4-one (190 mg, 821 μmol, 1.0 equiv) and 1-azido-4-nitrobenzene (175 mg, 1.07 mmol, 1.3 equiv; CAS RN 1516-60-5) in DMF (1.5 mL) under Ar was added ammonium acetate (317 mg, 4.11 mmol, 5.0 equiv) and the solution was stirred at 80° C. in a sealed tube for 15 h. The reaction mixture was purified by preparative HPLC (Gemini NX column) using a gradient of ACN:water (containing 0.1% TEA) (20:80 to 98:2) to furnish the desired compound as a light brown foam (55 mg, 26%). MS (ESI): m/z=257.2 $[M+H]^+$.

Step 4: rac-(1S,9R)-8-Oxa-3,4,5,11-tetrazatricyclo[7.3.0.02,6]dodeca-2(6),4-diene To a solution of rac-(1S,9R)-11-benzyl-8-oxa-3,4,5,11-tetrazatricyclo[7.3.0.0$^{2,6}$]dodeca-2(6),4-diene (113 mg, 441 μmol, 1.0 equiv) in MeOH (4 mL) was added Pd/C (27 mg, 25.4 μmol, 0.06 equiv; wt. 10%) and the mixture was stirred under an atmosphere of hydrogen (20 bar) at 60° C. for 36 h. The suspension was allowed to cool down to RT and filtered. The filtrate was completely evaporated to yield a colorless oil (73 mg, 100%) which was used in the next step without further purification. MS (ESI): m/z=167.1 $[M+H]^+$.

Example 11

A compound of formula (I) can be used in a manner known per se as the active ingredient for the production of tablets of the following composition:

| | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example 12

A compound of formula (I) can be used in a manner known per se as the active ingredient for the production of capsules of the following composition:

| | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

The invention claimed is:

1. A compound of formula (I):

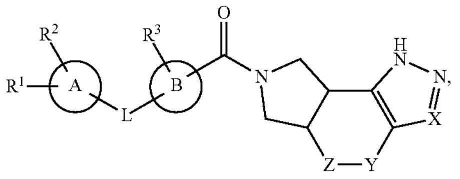

(I)

or a pharmaceutically acceptable salt thereof, wherein:

X is CH or N;

Y and Z are independently $CH_2$ or O, wherein at most one of Y and Z is O;

L is selected from a covalent bond, $—CHR^4—$, $—OCH_2—$, and $—CH_2O$;

A is selected from $C_6$-$C_{10}$-aryl and 5- to 10-membered heteroaryl;

B is a 4- to 7-membered heterocycle comprising 1-2 nitrogen atoms;

$R^1$ and $R^2$ are independently selected from hydrogen, halogen, $SF_5$, cyano, $C_{1-6}$-alkyl, $C_{1-6}$-alkoxy, halo-$C_{1-6}$-alkyl, halo-$C_{1-6}$-alkoxy, $C_6$-$C_{14}$-aryl, $C_3$-$C_{10}$-cycloalkyl, 5-14-membered heteroaryl, 3- to 14-membered heterocyclyl, $C_6$-$C_{14}$-aryloxy, $C_3$-$C_{10}$-cycloalkyloxy, 3- to 14-membered heterocyclyloxy, and 5-14-membered heteroaryloxy, wherein each of said 3- to 14-membered heterocyclyl, $C_6$-$C_{14}$-aryl, $C_3$-$C_{10}$-cycloalkyl, 5-14-membered heteroaryl, $C_6$-$C_{14}$-aryloxy, $C_3$-$C_{10}$-cycloalkyloxy, and 5-14-membered heteroaryloxy, are optionally substituted with 1-2 substituents selected from halogen, $C_{1-6}$-alkyl, $C_{1-6}$-alkoxy, halo-$C_{1-6}$-alkyl and halo-$C_{1-6}$-alkoxy; or $R^1$ and $R^2$, taken together with the atom(s) to which they are attached, form a 3- to 14-membered heterocycle that is optionally substituted with one or more $C_{1-6}$-alkyl;

$R^3$ is selected from hydrogen and $C_{1-6}$-alkyl; and $R^4$ is selected from hydrogen, $C_6$-$C_{14}$-aryl and halo-$C_6$-$C_{14}$-aryl.

2. The compound of formula (I) according to claim 1, or a pharmaceutically acceptable salt thereof, wherein:

X is CH or N;

Y is $CH_2$ or O; and

Z is $CH_2$.

3. The compound of formula (I) according to claim 1, or a pharmaceutically acceptable salt thereof, wherein:

L is selected from a covalent bond, —$CHR^4$—, and —$CH_2O$—;

A is $C_6$-$C_{10}$-aryl;

$R^1$ is selected from halogen, halo-$C_{1-6}$-alkyl, and $C_3$-$C_{10}$-cycloalkyl substituted with halo-$C_{1-6}$-alkyl;

$R^2$ is selected from hydrogen and halogen; and $R^4$ is hydrogen.

4. The compound of formula (I) according to claim 3, or a pharmaceutically acceptable salt thereof, wherein:

L is selected from a covalent bond and —$CH_2O$—;

A is $C_6$-$C_{10}$-aryl;

$R^1$ is selected from halo-$C_{1-6}$-alkyl, and $C_3$-$C_{10}$-cycloalkyl substituted with halo-$C_{1-6}$-alkyl; and $R^2$ is selected from hydrogen and halogen.

5. The compound of formula (I) according to claim 4, or a pharmaceutically acceptable salt thereof, wherein:

L is selected from a covalent bond and —$CH_2O$—;

A is phenyl;

$R^1$ is selected from $CF_3$ and (trifluoromethyl)cyclopropyl; and $R^2$ is selected from hydrogen and fluoro.

6. The compound of formula (I) according to claim 1, or a pharmaceutically acceptable salt thereof, wherein:

B is a 4- to 7-membered heterocycle comprising 1 nitrogen atom; and $R^3$ is hydrogen.

7. The compound of formula (I) according to claim 6, or a pharmaceutically acceptable salt thereof, wherein:

B is azetidinyl; and $R^3$ is hydrogen.

8. The compound of formula (I) according to claim 1, or a pharmaceutically acceptable salt thereof, wherein:

X is CH or N;

Y and Z are independently $CH_2$ or O, wherein at most one of Y and Z is O;

L is selected from a covalent bond, —$CHR^4$—, and —$CH_2O$—;

A is phenyl;

B is a 4- to 7-membered heterocycle comprising 1 nitrogen atom;

$R^1$ is selected from halogen, halo-$C_{1-6}$-alkyl, and $C_3$-$C_{10}$-cycloalkyl substituted with halo-$C_{1-6}$-alkyl;

$R^2$ is selected from hydrogen and halogen; and $R^3$ and $R^4$ are both hydrogen.

9. The compound of formula (I) according to claim 8, or a pharmaceutically acceptable salt thereof, wherein:

X is CH or N;

Y is $CH_2$ or O;

Z is $CH_2$;

L is selected from a covalent bond and —$CH_2O$—;

A is phenyl;

B is a 4- to 7-membered heterocycle comprising 1 nitrogen atom;

$R^1$ is selected from halo-$C_{1-6}$-alkyl, and $C_3$-$C_{10}$-cycloalkyl substituted with halo-$C_{1-6}$-alkyl;

$R^2$ is selected from hydrogen and halogen; and $R^3$ is hydrogen.

10. A compound of formula (I):

or a pharmaceutically acceptable salt thereof, wherein:

X is CH or N;

Y is $CH_2$ or O;

Z is $CH_2$;

L is selected from a covalent bond and —$CH_2O$—;

A is phenyl;

B is azetidinyl;

R is selected from $CF_3$ and (trifluoromethyl)cyclopropyl;

$R^2$ is selected from hydrogen and fluoro; and $R^3$ is hydrogen.

11. A compound or a pharmaceutically acceptable salt thereof, selected from:

[3-[[2-Fluoro-4-(trifluoromethyl)phenyl]methoxy]azetidin-1-yl]-[rac-(5aR,8aS)-4,5,5a,6,8,8a-hexahydro-1H-pyrrolo[3,4-g]indazol-7-yl]methanone;

[3-[[2-Fluoro-4-(trifluoromethyl)phenyl]methoxy]azetidin-1-yl]-[rac-(1S,9R)-7-oxa-3,4,11-triazatricyclo[7.3.0.02,6]dodeca-2 (6),4-dien-11-yl]methanone;

(−)- or (+)-[(1S,9R)-7-Oxa-3,4,11-triazatricyclo[7.3.0.02,6]dodeca-2 (6),4-dien-11-yl]-[3-[4-[1-(trifluoromethyl)cyclopropyl]phenyl]azetidin-1-yl]methanone;

(+)- or (−)-[(1R,9S)-7-Oxa-3,4,11-triazatricyclo[7.3.0.02,6]dodeca-2 (6),4-dien-11-yl]-[3-[4-[1-(trifluoromethyl)cyclopropyl]phenyl]azetidin-1-yl]methanone;

(−)- or (+)-[6-[(2,4-Difluorophenyl)methyl]-2-azaspiro[3.3]heptan-2-yl]-[(1S,9R)-7-oxa-3,4,11-triazatricyclo[7.3.0.02,6]dodeca-2 (6),4-dien-11-yl]methanone;

(+)- or (−)-[6-[(2,4-Difluorophenyl)methyl]-2-azaspiro[3.3]heptan-2-yl]-[(1R,9S)-7-oxa-3,4,11-triazatricyclo[7.3.0.02,6]dodeca-2 (6),4-dien-11-yl]methanone;

(−)- or (+)-[3-[[2-Fluoro-4-(trifluoromethyl)phenyl]methoxy]azetidin-1-yl]-[(5aR,8aS)-4,5,5a,6,8,8a-hexahydro-1H-pyrrolo[3,4-e]benzotriazol-7-yl]methanone;

(+)- or (−)-[3-[[2-Fluoro-4-(trifluoromethyl)phenyl]methoxy]azetidin-1-yl]-[(5aS,8aR)-4,5,5a,6,8,8a-hexahydro-1H-pyrrolo[3,4-e]benzotriazol-7-yl]methanone;

(−)- or (+)-[3-[[2-Fluoro-4-(trifluoromethyl)phenyl]methoxy]azetidin-1-yl]-[(1S,9R)-8-oxa-3,4,5,11-tetrazatricyclo[7.3.0.02,6]dodeca-2 (6),4-dien-11-yl]methanone; and (+)- or (−)-[3-[[2-Fluoro-4-(trifluoromethyl)phenyl]methoxy]azetidin-1-yl]-[(1R,9S)-8-oxa-3,4,5,11-tetrazatricyclo[7.3.0.02,6]dodeca-2 (6),4-dien-11-yl]methanone.

12. A process of manufacturing a compound of formula (I) according to claim 1, or a pharmaceutically acceptable salt thereof, the process comprising:

(a) reacting an amine of formula 2, wherein X, Y, and Z are as described in claim 1,

2

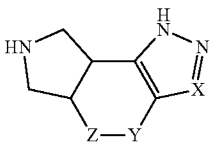

with a carboxylic acid 3a, wherein L, A, B, and $R^1$ to $R^3$ are as described in claim 1, 3a

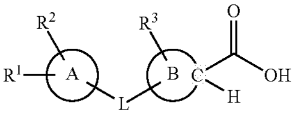

in the presence of a coupling reagent to form said compound of formula (IB), wherein X, Y, Z, L, A, B, and $R^1$ to $R^3$ are as defined in claim 1

(IB)

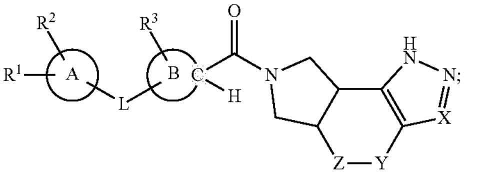

or (b) reacting an amine of formula 2, wherein X, Y, and Z are as described in claim 1,

2

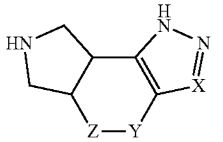

with a carboxylic acid chloride 3b, wherein L, A, B, and $R^1$ to $R^3$ are as described in claim 1

3b

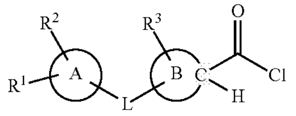

in the presence of a base to form said compound of formula (IB), wherein X, Y, Z, L, A, B, and $R^1$ to $R^3$ are as defined in claim 1;

or (c) reacting a first amine of formula 1, wherein A, B, L, and $R^1$ and $R^3$ are as described in claim 1,

1

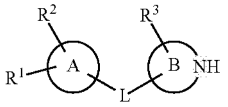

with a second amine 2, wherein X, Y, and Z are as described in claim 1

2

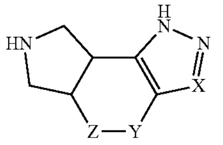

in the presence of a base and a urea forming agent, to form said compound of formula (IA), wherein X, Y, Z, L, A, B, and $R^1$ to $R^3$ are as defined in claim 1

(IA)

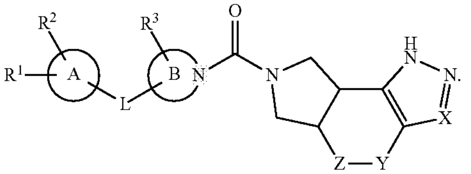

13. The process of claim 12, wherein:

the coupling reagent in process (a) is CDI, DCC, HATU, HBTU, HOBT, TBTU, $T_3P$ or Mukaiyama reagent, and the amine and carboxylic acid are further reacted in the presence of a base, wherein the base is TEA, DIPEA (Huenig's base) or DMAP; or the base in process (b) is TEA, Huenig's base, pyridine, DMAP or lithium bis(trimethylsilyl)amide; or the base in process (c) is sodium bicarbonate, and the urea forming reagent is bis(trichloromethyl) carbonate, phosgene, trichloromethyl chloroformate, (4-nitrophenyl) carbonate or 1,1'-carbonyldiimidazole.

14. A pharmaceutical composition, comprising a compound of formula (I) according to claim 1, or a pharmaceutically acceptable salt thereof, and a therapeutically inert carrier.

15. A pharmaceutical composition, comprising a compound of formula (I) according to claim 10, or a pharmaceutically acceptable salt thereof, and a therapeutically inert carrier.

16. A pharmaceutical composition, comprising a compound of claim 11, or a pharmaceutically acceptable salt thereof, and a therapeutically inert carrier.

17. The process of claim 12, part (a), wherein the coupling reagent is CDI, DCC, HATU, HBTU, HOBT, TBTU, T3P or Mukaiyama reagent.

18. The process of claim 12, part (a), further comprising the presence of a base selected from TEA, DIPEA (Huenig's base) and DMAP.

19. The process of claim 12, part (b), wherein the base is TEA, Huenig's base, pyridine, DMAP or lithium bis(trimethylsilyl)amide.

20. The process of claim 12, part (c), wherein the base is sodium bicarbonate and the urea forming reagent is bis(trichloromethyl) carbonate, phosgene, trichloromethyl chloroformate, (4-nitrophenyl) carbonate or 1,1'-carbonyldiimidazole.

* * * * *